(12) United States Patent
Deng et al.

(10) Patent No.: US 11,320,312 B2
(45) Date of Patent: May 3, 2022

(54) USER INTERFACE FOR DETERMINING LOCATION, TRAJECTORY AND BEHAVIOR

(71) Applicant: Butlr Technologies Inc, Burlingame, CA (US)

(72) Inventors: Honghao Deng, Belmont, CA (US); Jiani Zeng, Belmont, CA (US); Frances Jillian S. Qua, Jersey City, NJ (US)

(73) Assignee: BUTLR TECHNOLOGIES, INC., Burlingame, CA (US)

( * ) Notice: Subject to any disclaimer, the term of this patent is extended or adjusted under 35 U.S.C. 154(b) by 0 days.

(21) Appl. No.: 17/516,954

(22) Filed: Nov. 2, 2021

(65) Prior Publication Data

US 2022/0057270 A1 Feb. 24, 2022

Related U.S. Application Data

(63) Continuation-in-part of application No. 17/232,551, filed on Apr. 16, 2021, which is a continuation of (Continued)

(51) Int. Cl.
*G08B 13/08* (2006.01)
*G01J 5/00* (2022.01)
(Continued)

(52) U.S. Cl.
CPC ............ *G01J 5/0025* (2013.01); *G01J 5/12* (2013.01); *G16H 20/60* (2018.01); *G16H 40/67* (2018.01);
(Continued)

(58) Field of Classification Search
CPC .......... G01J 5/0025; G01J 5/12; G16H 40/67; G16H 20/60; G07C 9/00; A61B 5/01;
(Continued)

(56) References Cited

U.S. PATENT DOCUMENTS 8,718,748 B2 * 5/2014 Reinhold ............. H04N 13/243
600/473
9,274,204 B2 3/2016 Kim et al.
(Continued)

FOREIGN PATENT DOCUMENTS

WO 2016008430 2/2016
WO 2018056894 3/2018

OTHER PUBLICATIONS

Mikkilineni et al., "A novel occupancy detection solution using low-power IR-FPA based wireless occupancy sensor", Mar. 11, 2019, pp. 1-37, Energy and Buildings, Elsevier.
(Continued)

*Primary Examiner* — Toan N Pham
(74) *Attorney, Agent, or Firm* — Snell & Wilmer L.L.P.

(57) ABSTRACT

The system may include a setup app that is configured to locate, track and/or analyze activities of living beings in an environment. The system may be configured for determining a temperature of an object in a space, based on infrared (IR) energy data of IR energy from the object, determining location coordinates of the object in the space, comparing the location coordinates of the object to location coordinates of a fixture and determining that the object is a human being, in response to the temperature of the object being within a range, and in response to the location coordinates of the object being distinct from the location coordinates of the fixture.

20 Claims, 14 Drawing Sheets

Related U.S. Application Data application No. 17/178,784, filed on Aug. 18, 2021, now Pat. No. 11,022,495.

(60) Provisional application No. 62/986,442, filed on Mar. 6, 2020.

(51) Int. Cl.

| | | |
|---|---|---|
| *G01J 5/12* | (2006.01) | |
| *G16H 20/60* | (2018.01) | |
| *G16H 40/67* | (2018.01) | |
| *G06Q 10/08* | (2012.01) | |
| *H04W 84/18* | (2009.01) | |
| *G06F 30/13* | (2020.01) | |
| *G06F 9/54* | (2006.01) | |
| *A61B 5/01* | (2006.01) | |
| *A61B 5/16* | (2006.01) | |
| *A61B 5/11* | (2006.01) | |
| *G07C 9/00* | (2020.01) | |

(52) U.S. Cl.
CPC ............... *A61B 5/01* (2013.01); *A61B 5/1118* (2013.01); *A61B 5/16* (2013.01); *G06F 9/541* (2013.01); *G06F 30/13* (2020.01); *G06Q 10/087* (2013.01); *G07C 9/00* (2013.01); *H04W 84/18* (2013.01)

(58) Field of Classification Search
CPC ........ A61B 5/1118; A61B 5/16; H04W 84/18; G06F 30/13; G06F 9/541; G06Q 10/087
See application file for complete search history.

(56) References Cited

U.S. PATENT DOCUMENTS

| 10,019,962 | B2 | 7/2018 | Liu et al. | |
|---|---|---|---|---|
| 11,022,495 | B1* | 6/2021 | Deng | G16H 20/30 |
| 2001/0006367 | A1* | 7/2001 | Oda | G08B 13/19 |
| | | | | 340/567 |
| 2016/0195856 | A1 | 7/2016 | Spero | |
| 2018/0150903 | A1 | 5/2018 | Waldron et al. | |
| 2020/0074175 | A1* | 3/2020 | Zheng | G06K 9/6289 |
| 2020/0077892 | A1 | 3/2020 | Tran | |
| 2020/0175330 | A1 | 6/2020 | Wang et al. | |

OTHER PUBLICATIONS

Chen et al., "Unobtrusive Sensor based Occupancy Facing Direction Detection and Tracking using Advanced Machine Learning Algorithms", IEEE Sensors Journal, Aug. 1, 2018, pp. 1-9, vol. 18, Issue: 15.

Chen et al., "A fall detection system based on infrared array sensors with tracking capability for the elderly at home", 2015 17th International Conference on E-health Networking, Application & Services, (HealthCom), Department of Electiical Engineering, National Tsing Hua University, Apr. 19, 2015, pp. 428-434, Hsinchu, Taiwan.

Berry, Park, "A Passive System for Quantifying Indoor Space Utilization", ACADIA 2017, Disiplines + Disruption, pp. 138-145.

Shetty et al. "Detection and tracking of a human using the infrared thermopile array sensor—"Grid-EYE"", 2017 International Conference on Intelligent Computing, Instrumentation and Control Technologies, ICICICT, 2017, pp. 1490-1495.

Yun et al., "Detecting direction of movement using pyroelectric infrared sensors", IEEE Sensors Journal, May 2014, pp. 1482-1489, vol. 14, No. 5.

Hao, "Multiple Human Tracking and Identification With Wireless Distributed Pyroelectric Sensors", 2006, Dissertation submitted—Department of Electrical and Computer Engineering—Duke University, pp. 1-184.

Yuan et al., "Human indoor location for binary infrared sensor tracking system: On improved credit and dynamic pruning algorithm", ISA Transactions, Apr. 19, 2019, pp. 1-9, Published by Elsevier Ltd on behalf of ISA.

USPTO, Notice of Allowance dated Apr. 15, 2021 in U.S. Appl. No. 17/178,784.

Honghao Deng, et al., U.S. Appl. No. 17/178,784, filed Feb. 18, 2021 entitled "Monitoring Human Location, Trajectory and Behavior Using Thermal Data," 62 pages.

Honghao Deng, et al., U.S. Appl. No. 17/232,551, filed Apr. 16, 2021 entitled "Thermal Data Analysis for Determining Location, Trajectory and Behavior," 50 pages.

\* cited by examiner

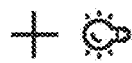
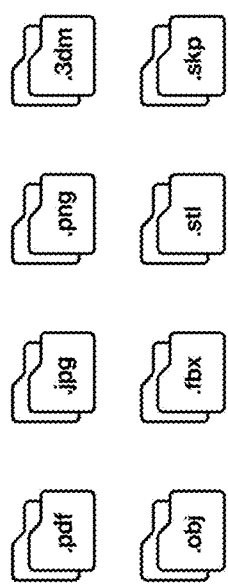
FIGURE 8A

USER INTERFACE FOR DETERMINING LOCATION, TRAJECTORY AND BEHAVIOR

CROSS-REFERENCE TO RELATED APPLICATIONS

This application is a continuation-in-part of, and claims priority to, and the benefit of, U.S. Ser. No. 17/232,551 filed on Apr. 16, 2021 and entitled "THERMAL DATA ANALYSIS FOR DETERMINING LOCATION, TRAJECTORY AND BEHAVIOR". U.S. Ser. No. 17/232,551 is a continuation of U.S. Ser. No. 17/178,784 filed Feb. 18, 2021 and entitled "MONITORING HUMAN LOCATION, TRAJECTORY AND BEHAVIOR USING THERMAL DATA" (aka U.S. Pat. No. 11,022,495 issued Jun. 1, 2021. U.S. Ser. No. 17/178,784 claims priority to U.S. Provisional Ser. No. 62/986,442 filed Mar. 6, 2020 and entitled "MULTI-WIRELESS-SENSOR SYSTEM, DEVICE, AND METHOD FOR MONITORING HUMAN LOCATION AND BEHAVIOR." All of which are hereby incorporated by reference in their entirety for all purposes.

FIELD

This disclosure generally relates to a user interface for a system that is configured for locating, tracking and analyzing human activities in an environment.

BACKGROUND

While some businesses may try to use basic machines to count the number of people that enter and exit a particular door that leads to a store, such information is very limited for analyzing the actions of those people within the store. Businesses may be very interested in better understanding the movements, trajectories and activities of customers within their stores. For example, a business may be interested to know if a certain display in a particular aisle in the store attracted more customers to that aisle. Moreover, a business may be interested to know how many customers that walked down aisle #4 also walked down aisle #5 and how many customers that walked down aisle #4 skipped aisle #5, and instead next walked down aisle #6. Such data can help a business optimize its operations and maximize its profits.

Businesses may also be interested in more fully understanding the general traffic patterns in their store in relation to time. To help a business better allocate its own resources and optimize its business relations with collaborating third-parties, a business may want to understand traffic patterns during the busiest times throughout a day, during the busiest days within a week, during a particular month and/or during a particular year. Moreover, to help recognize unusual behaviors and/or to detect accidents in real time, a business may want to have more information about the spatial and/or temporal patterns of traffic and occupancy levels.

Furthermore, to analyze resident well-being and to determine whether the resident is qualified to live independently, assisted living providers often want to obtain tenants' spatial and temporal movement data. For example, providers may want to analyze tenants' moving speed based on the tenants' indoor location throughout time, calculate total calories expended based on the tenants' movement, and/or monitor the tenants' body temperature.

SUMMARY

The method may include determining a temperature of an object in a space, based on infrared (IR) energy data of IR energy from the object, determining location coordinates of the object in the space, comparing the location coordinates of the object to location coordinates of a fixture and determining that the object is a human being, in response to the temperature of the object being within a range, and in response to the location coordinates of the object being distinct from the location coordinates of the fixture.

The method may further include counting the human being in at least one of a headcount or occupancy in the space, in response to the human being crossing a door line. The method may further include determining that the object is not a human being, in response to at least one of the temperature of the object being outside of the range or the location coordinates of the object overlapping with the location coordinates of the fixture. The method may further include receiving the location coordinates of the fixture in the space. The method may further include comprising determining that the object is a human being, based on a fixture type of the fixture. The method may further include determining that the object is a human being, based on an orientation of the fixture. The method may further include determining that the object is a human being, based on movement of the object. The method may further include auto-aligning the object by automatically moving the object to an edge of a nearby object that is similar to the object. The method may further include adjusting a temperature delta between a temperature of the object and a temperature of the space. The method may further include determining a trajectory of the object based on changes of the temperature in pixels, wherein the temperature is projected onto a grid of the pixels. The method may further include displaying the object in a virtual space that replicates the space. The method may further include displaying a trajectory of the object in a virtual space that replicates the space, wherein the trajectory of the object is displayed at least one of frame by frame or with visualization smoothing. The method may further include displaying a dwell time of the object in the space. The method may further include displaying a posture of the human being in the space, based on a pose of the human being.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

FIGS. 8A and 8B is an exemplary user interface, prompting the user to upload to the application any specific file that may work as supplementary visual information to the representation of their physical space, in accordance with various embodiments.

DETAILED DESCRIPTION

In various embodiments, the system is configured to locate, track and/or analyze activities of living beings in an environment. The system does not require the input of personal biometric data. While the disclosure may discuss human activities, the disclosure contemplates tracking any item that may provide infrared (IR) energy such as, for example an animal or any object. While the disclosure may discuss an indoor environment, the system may also track in an outdoor environment (e.g., outdoor concert venue, outdoor amusement park, etc.) or a mixture of outdoor and indoor environments.

Figure 1A:
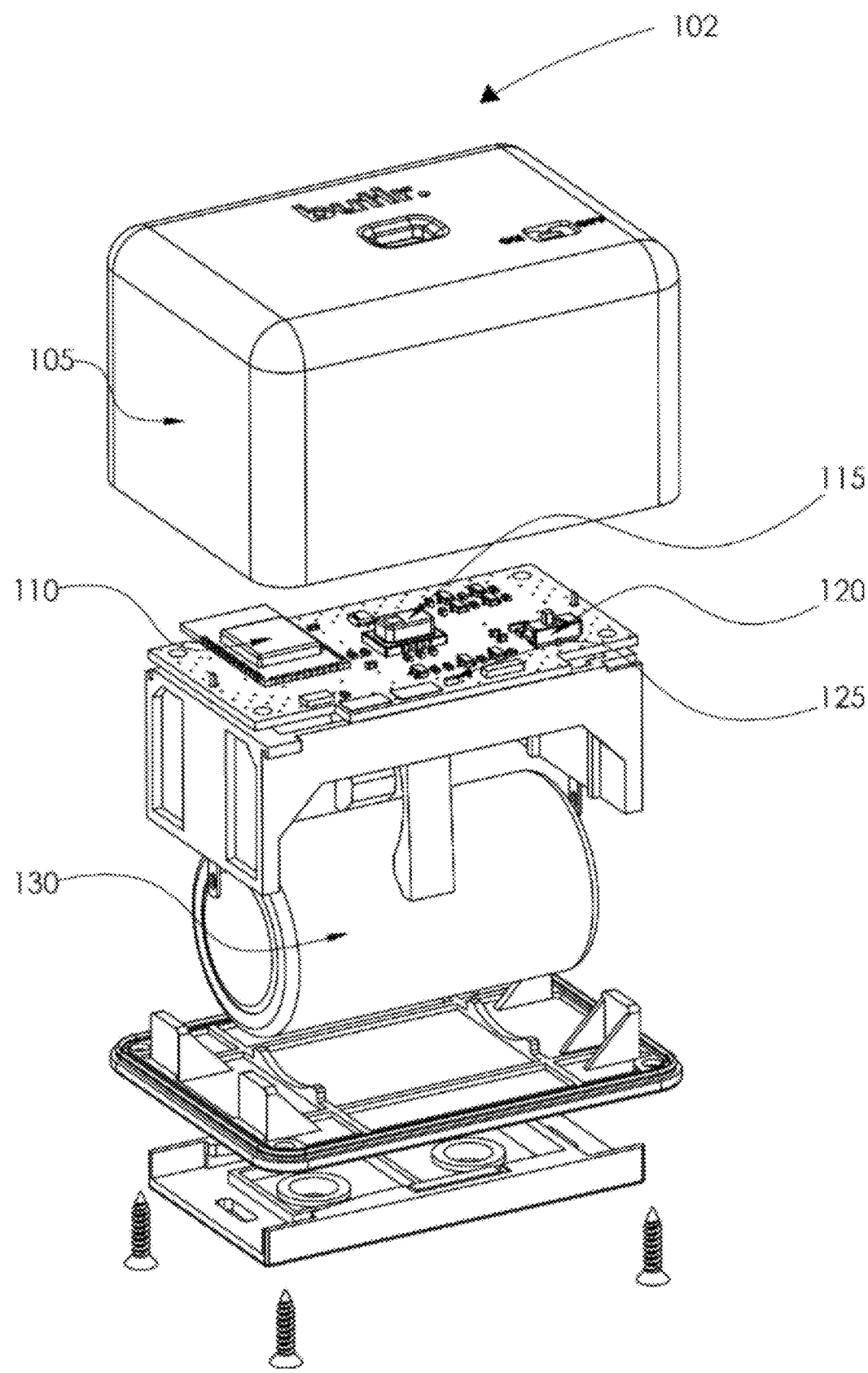
FIG. 1A is an exemplary schematic diagram of the main components of a sensor node, which are parts of the overall system, in accordance with various embodiments.
Figure 1B:
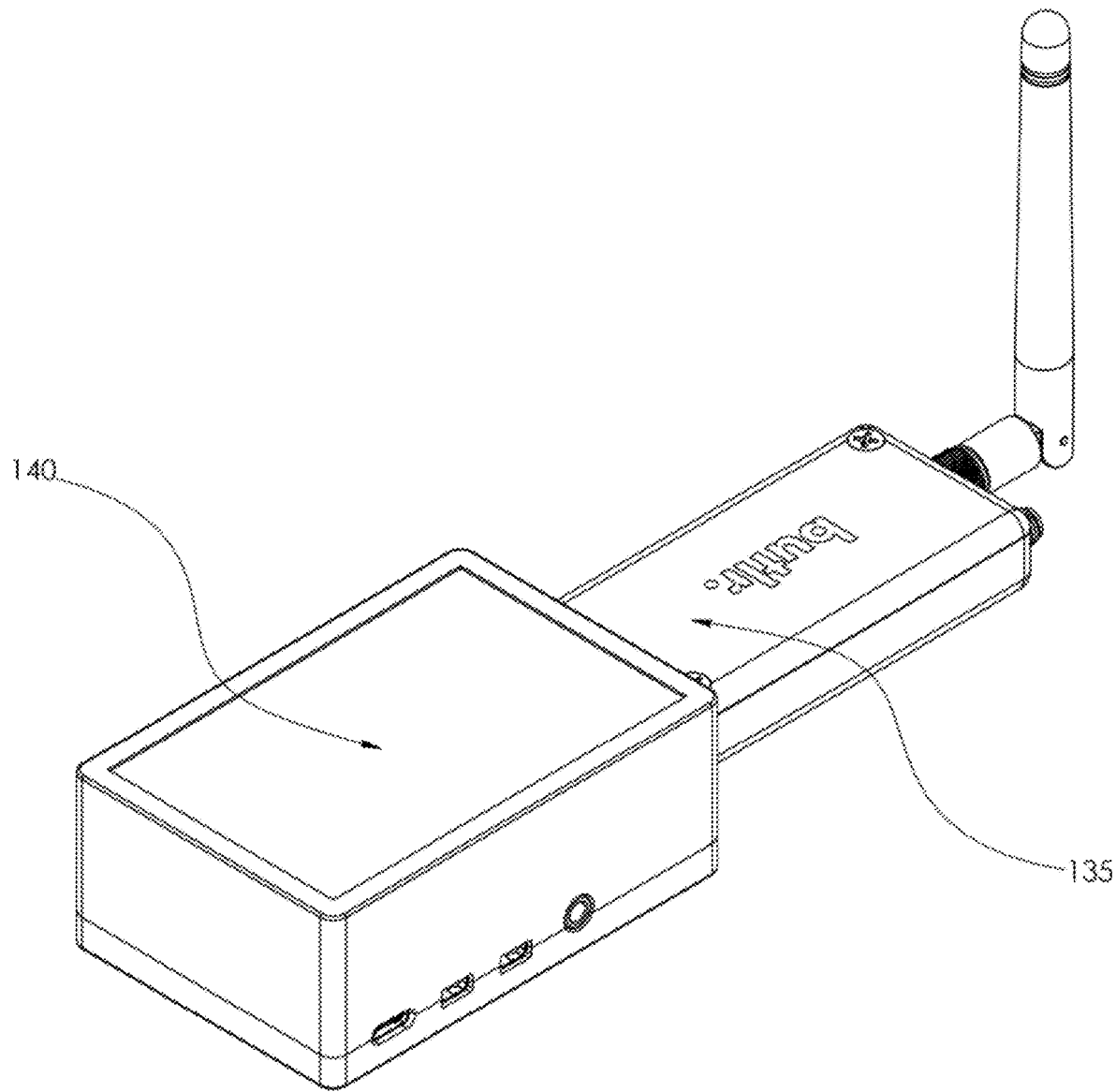
FIG. 1B is an exemplary schematic diagram of a gateway and a microprocessor, which are parts of the overall system, in accordance with various embodiments.
Figure 3:
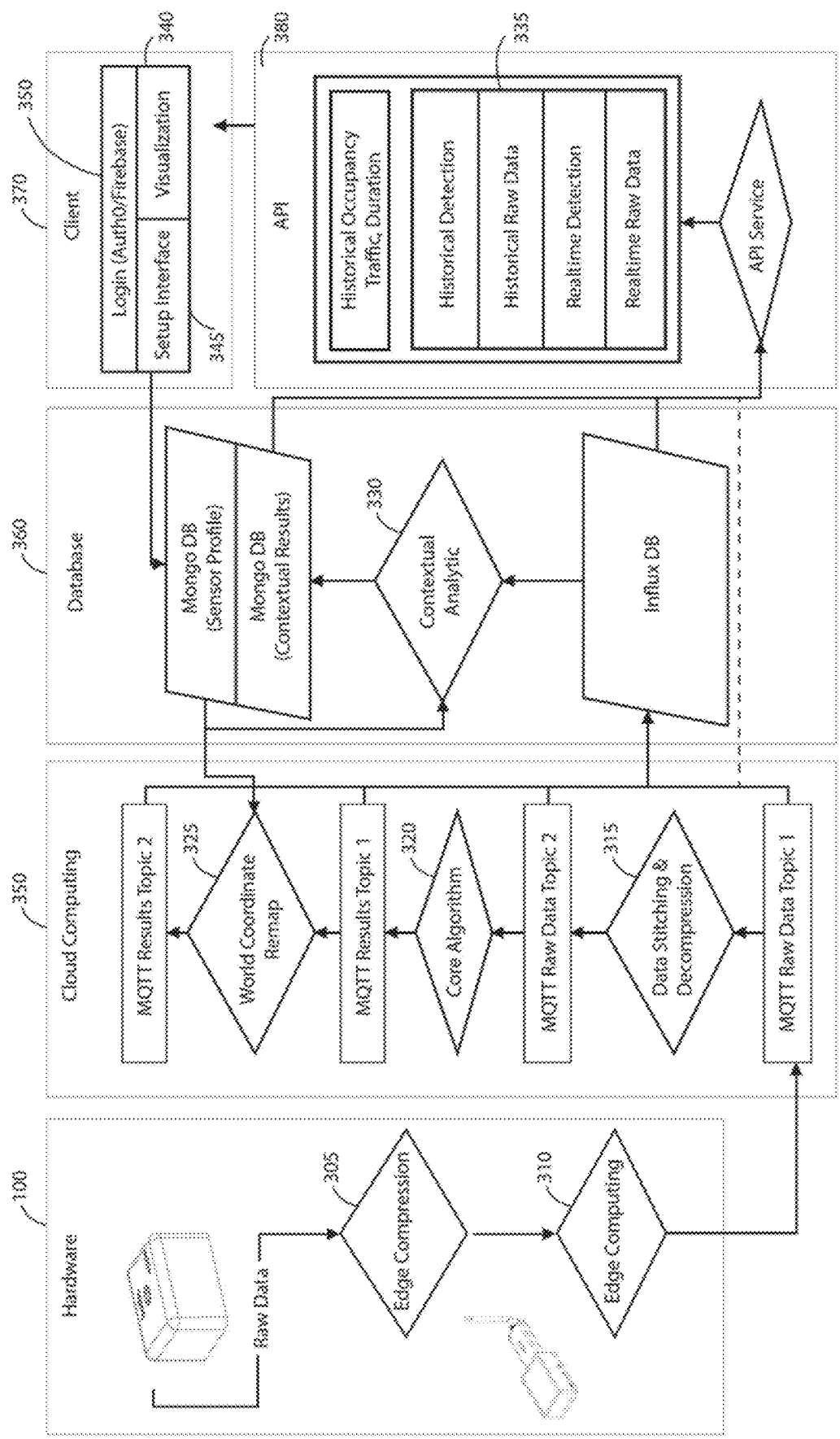
FIG. 3 is an exemplary system architecture, in accordance with various embodiments.

As set forth in more detail in FIGS. 1A, 1B and 3, in various embodiments, the system may include a plurality of sensor nodes 102, a gateway 135, a microprocessor 140, a computing module 350 (e.g., a cloud computing module), a database 360 and/or a user interface 370 (e.g., FIGS. 4A, 4B, 7, 8, 9 and 10). Each sensor node 102 may comprise an enclosure 105, an antenna 110, a sensor module 115, a switch 120, a light emitting diode (LED) 125 and a power source 130.

In various embodiments, the sensor module 115 may be any type of sensor such as a thermopile sensor module. The thermopile sensor module 115 may include, for example, a Heimann GmbH sensor module or Panasonic AMG8833. Each sensor module 115 may be housed in an enclosure 105. The sensor module 115 is configured to measure temperature from a distance by detecting the IR energy from an object (e.g., living being). If the living being has a higher temperature, then the living being will emit more IR energy. The thermopile sensing element in the thermopile sensor module 115 may include thermocouples on a silicon chip. The thermocouples absorb the IR energy and produce an output signal indicative of the amount of IR energy. As such, a higher temperature causes more IR energy to be absorbed by the thermocouples resulting in a higher signal output.

In various embodiments, the sensor node 102 interfaces may be wireless to help reduce the labor costs and materials costs associated with the installation. In various embodiments, each of the sensor nodes 102 may obtain power from any power source 130. The power source 130 may power one or more sensor nodes 102. Each of the sensor nodes 102 may be separately battery-powered. The batteries may be sufficiently low-powered to work for more than 2 years with a single battery (e.g., 19wh battery). The battery 130 may include a battery from any manufacturer and/or a PKCELL battery, D-cell battery or any other battery type. The battery 130 may be contained within a battery holder (e.g., Bulgin battery holder). The system may also measure the battery voltage of the battery 130 (e.g., D-cell battery). The battery voltage may be measured using an analog-digital converter that is located onboard with the antenna 110 (e.g. Midatronics Dusty PCB antenna). The system may also add a timestamp to the battery voltage data when the battery voltage measurement is acquired.

The system may be scalable to a larger footprint by adding more sensor nodes 102 to the sensor nodes 102 array. In various embodiments, the sensor nodes 102 may be added dynamically, wherein an exemplary user interface for adding a sensor is set forth in FIG. 7. In particular, the user may add or remove sensor nodes 102 from an established network of sensor nodes 102 at any time or at any location. The sensor nodes 102 may be located anywhere, so long as the sensor nodes 102 location is in the gateway's 135 bandwidth. As such, a larger number of sensor nodes 102 may form a mesh network to communicate with the gateway 135. The sensor nodes 102 may communicate with the gateway 135 at about the same time. Each new sensor node 102 connected to the gateway 135 may further extend the boundary of the mesh network, improves system stability and improves system performance. As such, a larger number of sensor nodes 102 may form a mesh network to communicate with the gateway 135. The sensor nodes 102 may communicate with the gateway 135 at about the same time. Each new sensor node 102 connected to the gateway 135 further extends the boundary of the mesh network, improves system stability and improves system performance. The sensor nodes 102 may be mounted on or installed on any portion of the building or on any object. For example, the sensor nodes 102 may be installed into the ceiling, sidewall or floor of a desired space using any fastener known in the art. The distance between the sensor nodes 102 may be, for example, 4 meters apart for a ceiling that is 2.5 meters high.

Figure 6:
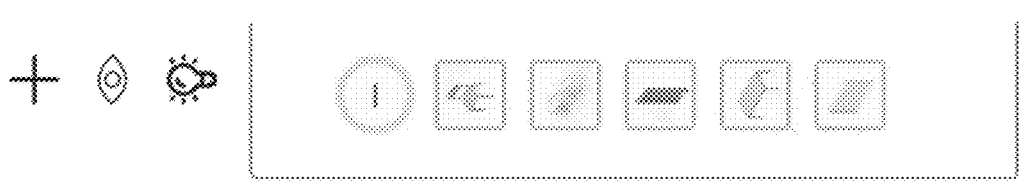
FIG. 6 is an exemplary building layout showing certain sensor nodes and area of coverage for each sensor node, in accordance with various embodiments.
Figure 6:
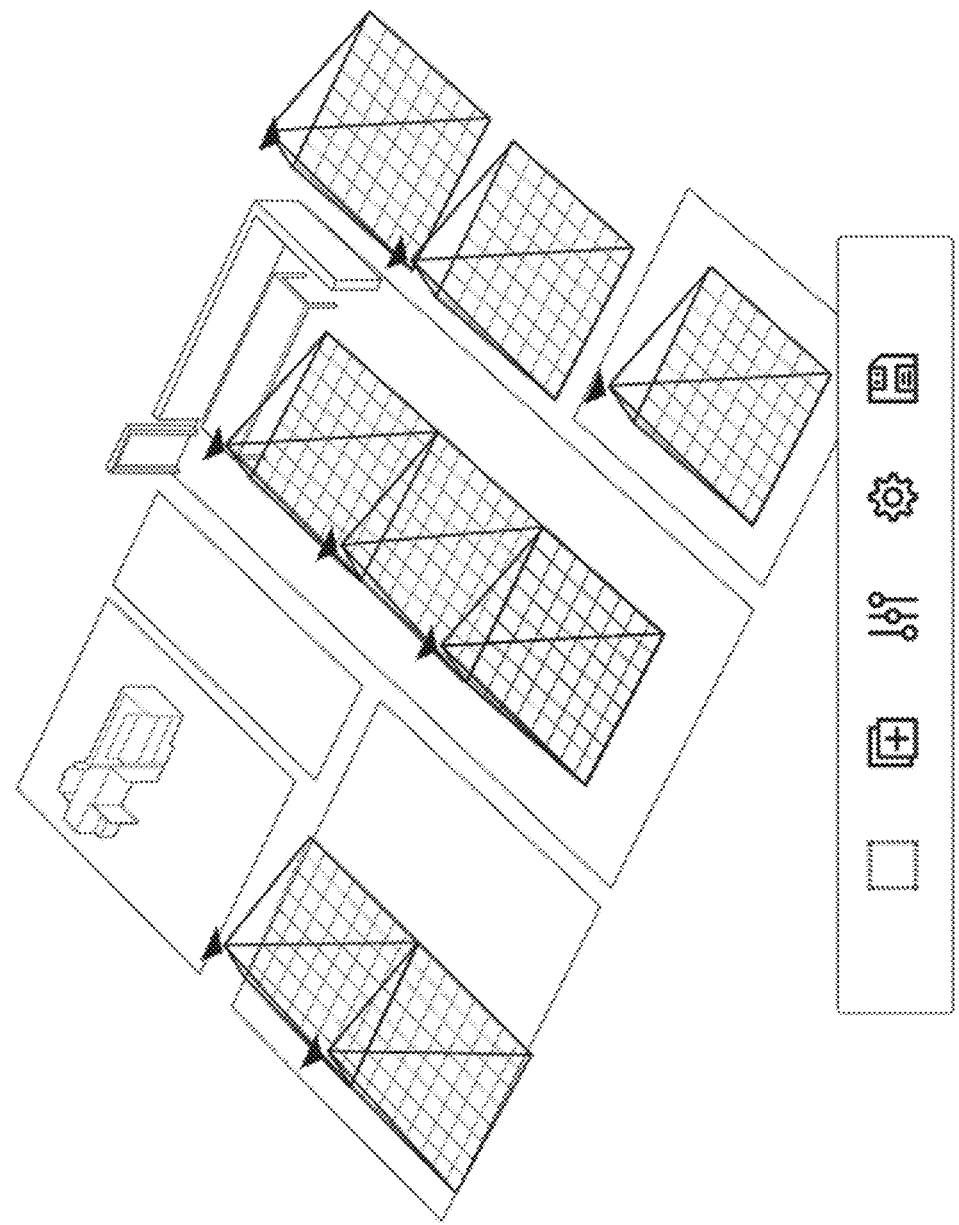

In various embodiments, each sensor node 102 installed in any given space may have a unique number (e.g., MAC address) assigned to the sensor node 102. The system uses the unique number to create a structured network with numbered sensor nodes 102. As shown in FIG. 6, each sensor node may cover a different area and carry this unique number which is accessed by the user both in the digital environment and also in the physical environment. In particular, the unique number is clearly printed on the enclosure 105 of the sensor node and declared in the user's screen when the user is installing the sensor node. This way, the user can identify if the location of their physical sensor node matches the digital representation in the electronic space they have created in the installation application.

Figure 7:
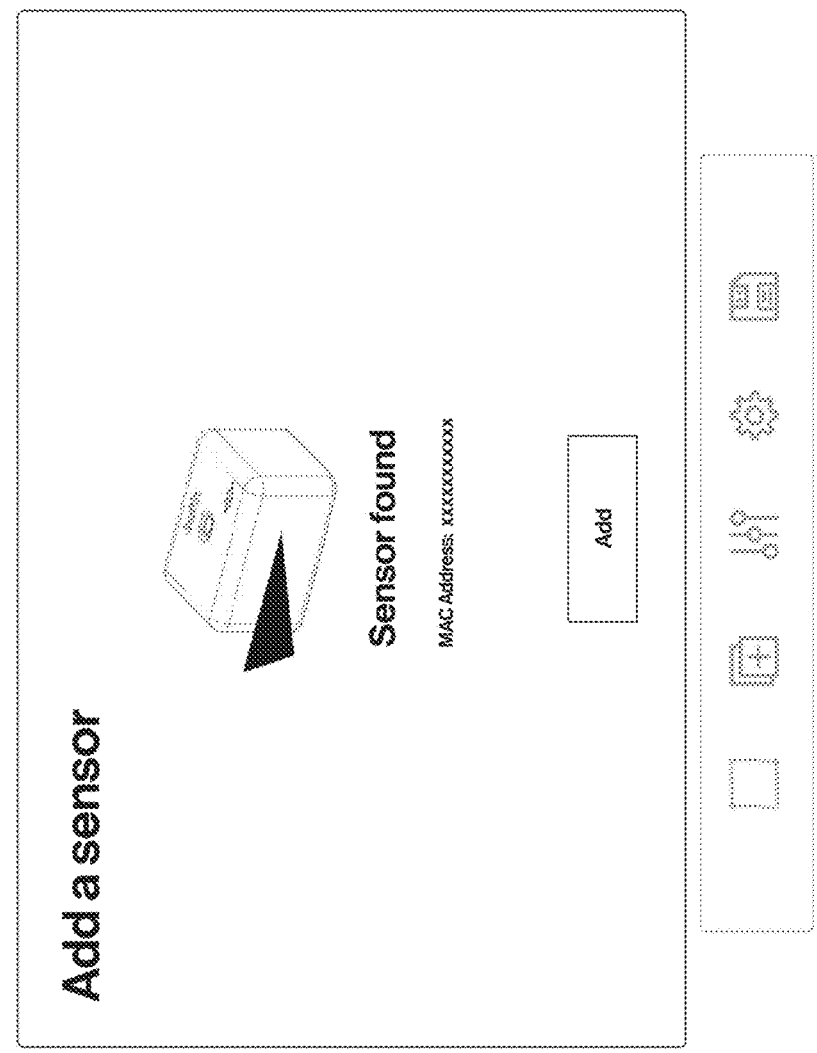
FIG. 7 is an exemplary user interface, showing the response of the application to the detection of a sensor node in the physical space, after the user has successfully logged in the sensor node, in accordance with various embodiments.
Figure 8B:
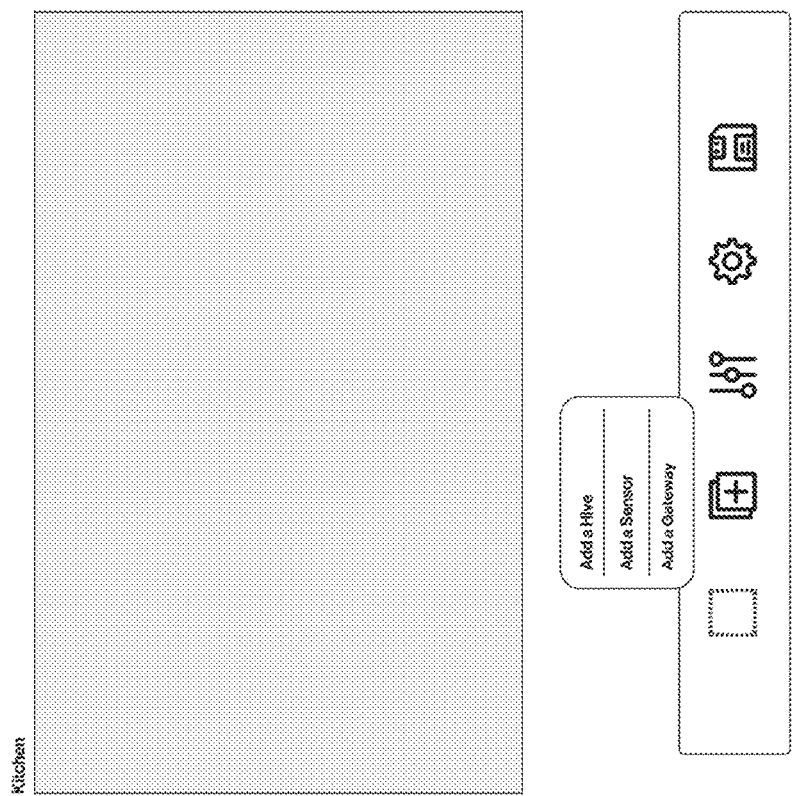

After the sensor node 102 is added and setup in the system, as set forth in FIGS. 7 and 8B, the sensor node 102 creates a profile. The user is prompted to either scan a QR code located on the sensor, thus automatically registering the digital representation of the physical sensor, or manually type in the MAC address of the sensor in question. The sensor node 102 profile may include the sensor node 102 height, mac address, relative location in space, surrounding objects and/or context information. The system determines the extent of coverage for each sensor node based on the sensor node's 102 height that the user inputs as information in its profile. Some examples of context information may include the name of the room the sensor is located in, a name for the sensor itself (if the user wishes to assign one) and the number assigned to the sensor. The user may upload files about the surrounding environment, as shown in FIG. 8A. Such files may include, for example, a PDF, JPG, PNG, 3DM, OBJ, FBX, STL and/or SKP. The surrounding information may include furniture within the sensor node 102 field, architectural layout around the sensor node 102 field, etc. The user may have the discretion to add surrounding objects within the space. The sensor node may not register the surrounding objects; however, the surrounding objects may provide a more rich visual context for the user's own personal use. The sensor node 102 profile may be stored in the users' profile in the database 360.

The thermopile sensor module 115 may project the temperature of an object onto a grid. The grid may be an 8 pixels×8 pixels grid, 16 pixels×16 pixels grid, or 32 pixels× 32 pixels grid (64 pixels, 256 pixels, or 1024 pixels, respectively). The thermopile sensor module 115 may be tuned to detect specific heat spectra to allow for the detection of objects with standard temperature (e.g. the human body). The average normal body temperature is generally accepted as 98.6° F. (37° C.). However, the normal body temperature can have a wide range from 97° F. (36.1° C.) to 99° F. (37.2° C.). A higher temperature most often indicates an infection or illness. The system may detect such differences in temperature because the sensor module 115 may have an accuracy of 0.5° C. In the case of multiple human bodies being in the same area, the thermopile sensor module 115 captures and processes each body as a distinct source of heat. In particular, the system avoids overlapping body temperature readings from different bodies by including a calibration process that is built into the 3D front end (exemplary user interface is shown in FIG. 10).

Figure 10:
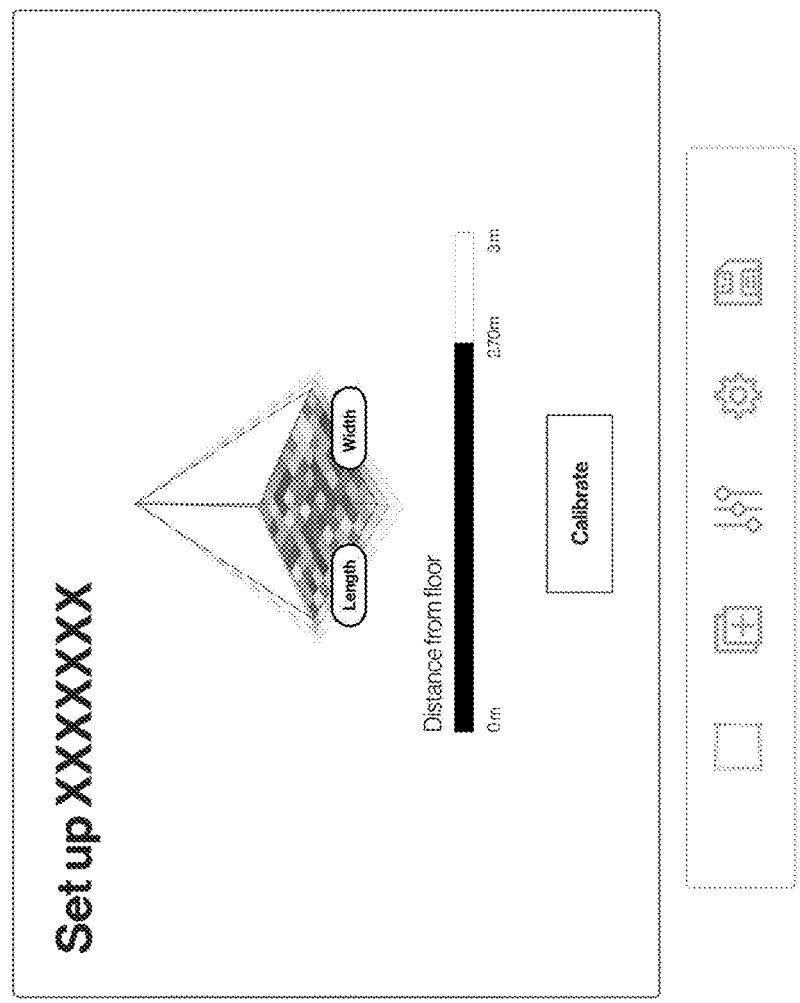
FIG. 10 is an exemplary user interface, showing the ability to set-up and calibrate a sensor node, in accordance with various embodiments.

As part of the calibration process (exemplary user interface is shown in FIG. 10), the user is asked through the application's interface to step out of all sensor modules' 115 coverage, so that the system can automatically adjust the sensitivity of the sensor modules 115. Starting with maximum sensitivity, the system gradually decreases its sensitivity until there is no high-frequency detection of noise anymore. The absolute elimination of noise allows for the detection of a body as a distinct source of heat and, subsequently, the detection of two heat sources such as human bodies as distinct and separate entities. For spatial overlapping readings between two sensor modules' 115 "field of view", during the calibration process, the system recognizes overlapping areas between two sensor modules 115 and averages the common detections between the two sensor modules 115. In case there are overlaps detected between more than two sensor modules 115, the system averages the overlaps for each pair sequentially. For example, for an overlap between sensor modules 115 A, B and C, the system averages A and B, then proceeds to average the result of AB with C.

If automatic calibration fails during the calibration process (exemplary user interface is shown in FIG. 10), the system automatically generates a digital path between the installed sensor nodes, prompting the user to physically stand below each sensor node. When doing so, the sensor node 102 detects the user's movement and the detection becomes visible inside the application. If successful, the user is prompted to follow the path and thus complete the calibration for each sensor node 102 of the network. Should any sensor not respond as mentioned above, the user is prompted to digitally manipulate the sensitivity of the sensor module 115 by sliding a digital bar and adjusting the sensitivity levels of the sensor node in question accordingly. More specifically, during the troubleshooting of the calibration process, the user is prompted to stand below the physical sensor, at each four corners of its field-of-view— one at a time. At each corner, named A, B, C and D by default in the app, the user is called to stay as long as the system detects their presence and successfully prints it on the sensors' digital double. Once the location is detected, the application asks the user which of the four possible corners they are trying to mark.

In various embodiments, the thermopile sensor modules 115 may detect an array of temperature readings. In addition to detecting the temperature of a living being based on the pixel values, the thermopile sensor module 115 may also obtain the temperature of the environment where the sensor module 115 is located. The system uses both local and global information—both each pixel individually and all sensors modules' 115, forming the network, pixels in total—to determine what the background temperature field is. The thermopile sensor module 115 may obtain an independent temperature measurement of the sensor node 102 itself. The temperature of the sensor module 115 may be obtained using an onboard thermal couple. The system may use the temperature of sensor node 102 and/or the temperature of the sensor module 115 to give an assessment of the temperature profile of the space being monitored. The onboard thermal couple measurement itself measures the temperature of the space at the location of the sensor. The system uses bilinear interpolation to estimate the temperature between sensor nodes 102 and/or sensor modules 115 in space to approximate the temperature distribution. Moreover, in various embodiments, the system may measure and capture the temperature of the environment multiple times throughout the day in order to reduce the adverse effect of keeping a fixed background temperature field for threshold calculation, thus increasing the accuracy of the overall detection in real world scenarios where the environmental temperature is dynamic.

In various embodiments, the plurality of sensor nodes 102 may provide information in real-time to help produce real-time location, trajectory and/or behavior analysis of human activities. By employing multiple sensor nodes 102, and based on the density of the network, the system can deduce the trajectory of any moving object detected by the sensor node 102. As mentioned above, the thermopile sensor module 115 inside the sensor node is designed to measure temperature from a distance by detecting an object's infrared (IR) energy. The higher the temperature, the more IR energy is emitted. The thermopile sensor module 115, composed of small thermocouples on a silicon chip, absorbs the energy and produces an output signal. The output signal is a small voltage which is proportional to the surface temperature of the IR emitting object in front of the sensor. Each thermopile sensor module 115 has 64 thermopiles, each of which is sensitive to the IR energy emitted by an object. To determine the trajectory, in various embodiments, each sensor module 115 divides the area captured by the sensor module 115 into a number of pixels, organized in a rectangular grid, in the direction aligned with the 64 thermopiles, each of which is associated with one 8×8 part of the aforementioned grid. The system monitors for serial changes in the temperature of sequential pixels. The system determines that such serial changes are indicative of the movement of a living being. The system logs such movement as the formation of a trajectory in space. The more nodes in the network, the more accurate the deduction is about the trajectories, as the trajectories detected are uninterrupted by "blind spots."

The computational engine analyzes the human behavior and trajectories. For example, with respect to occupancy control, the system may compute the total number of people in a space to compare with the occupancy requirement established. The system identifies all of the heat sources in the space monitored by the sensor module 115 and adds the number of all the heat sources that are generated by people.

With respect to occupant temperature screening, the system may detect the presence of a person by capturing the person's body heat. Temperature screening may include an automatic adjustment to the sensitivity of the sensor module 115 once such detection is detected. It should be noted that temperature screening may be different than body location detection. Body temperature screening means to detect an elevated body temperature of the person detected, such that the sensitivity requirement is higher than just body location detection.

With respect to monitoring the occupant's body temperature, the system 100 may be able to obtain the user's body temperature in the close field of one (1) meter from the sensor node 102, through reading the temperature of the region near the eye socket using the more detailed 32×32 grid in the sensor module 115. For the system to locate the eye sockets, the user may be asked to directly stare at the sensor node 102, allowing the sensor module 115 to detect the highest-in-temperature pixels.

With respect to analyzing occupant moving speed, the system may log the movement of a person under the network of sensor nodes 102. A series of 'waypoints' are produced in accordance with time. The system uses the distance traveled based on the waypoint information and the time it takes to travel said distance in order to calculate the movement speed of the user in question.

With respect to calculating total calories burnt based on the occupant's movement, the user inputs information such as the occupant's weight, gender and age, through the interface 370 to the system. The system may use the movement speed and distance captured (as mentioned above) in order to calculate the rough calories burnt during the time of captured movement.

Figure 4A:
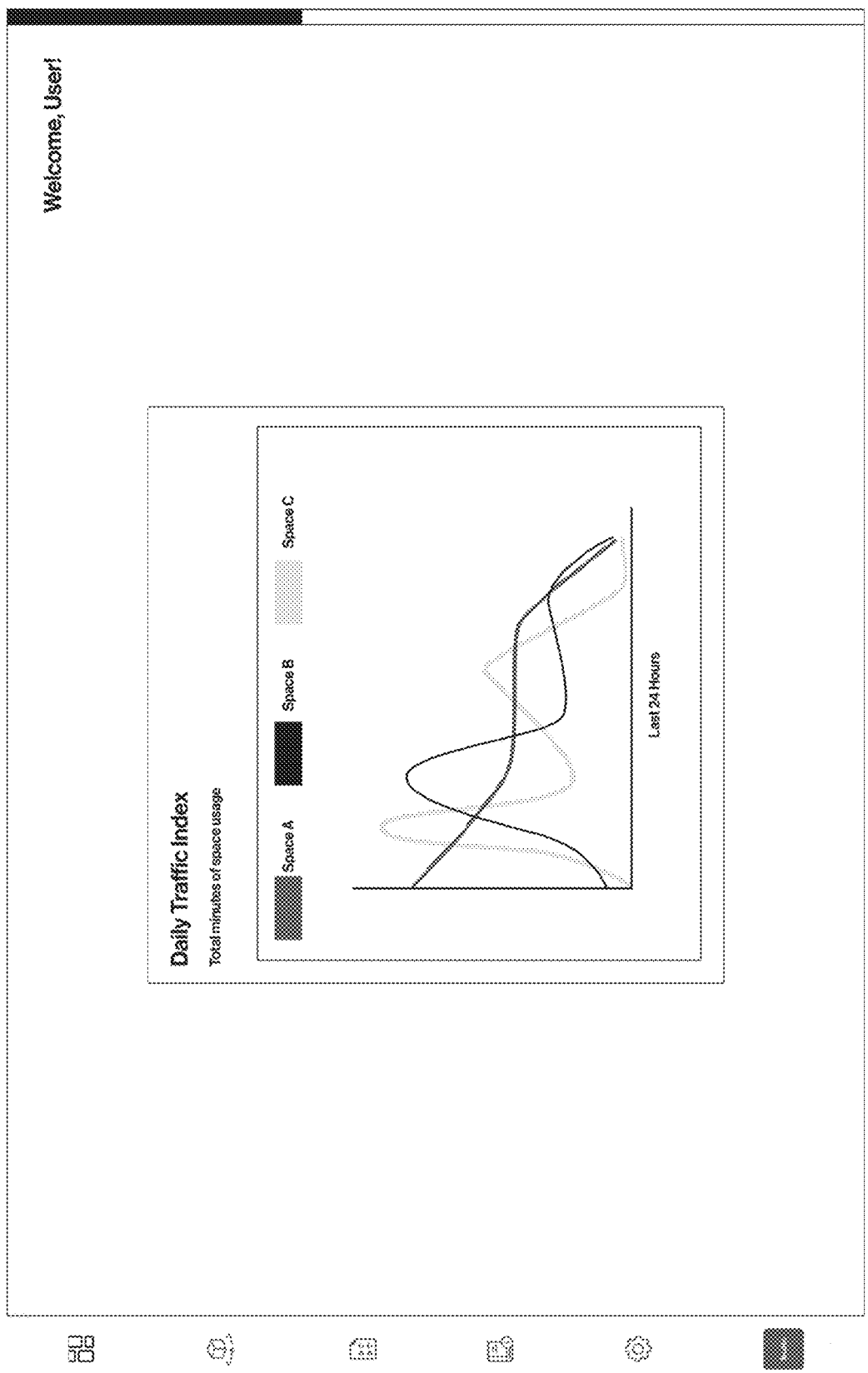
FIGS. 4A and 4B are exemplary user interfaces, in accordance with various embodiments.
Figure 4B:
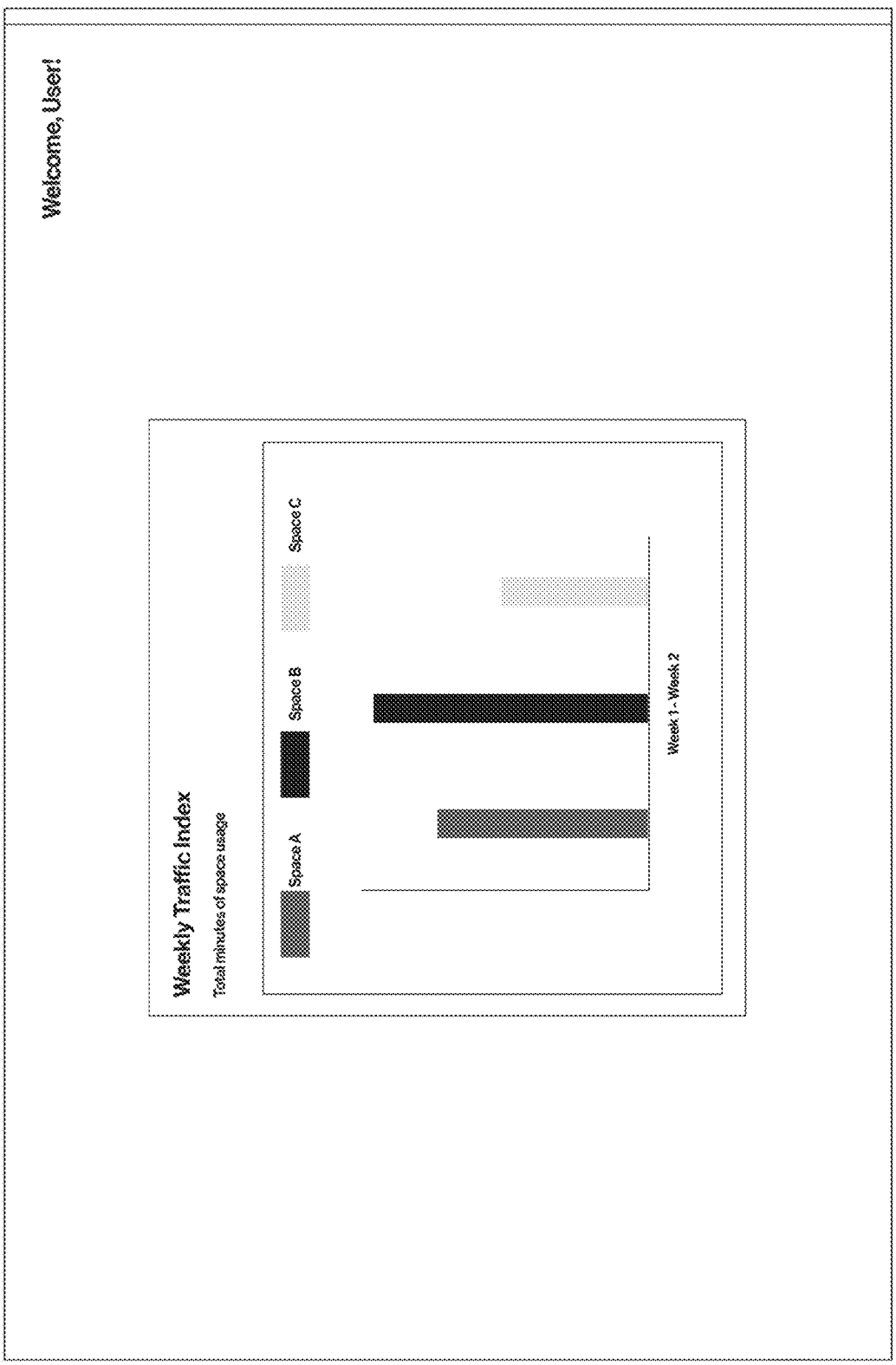
Figure 5:
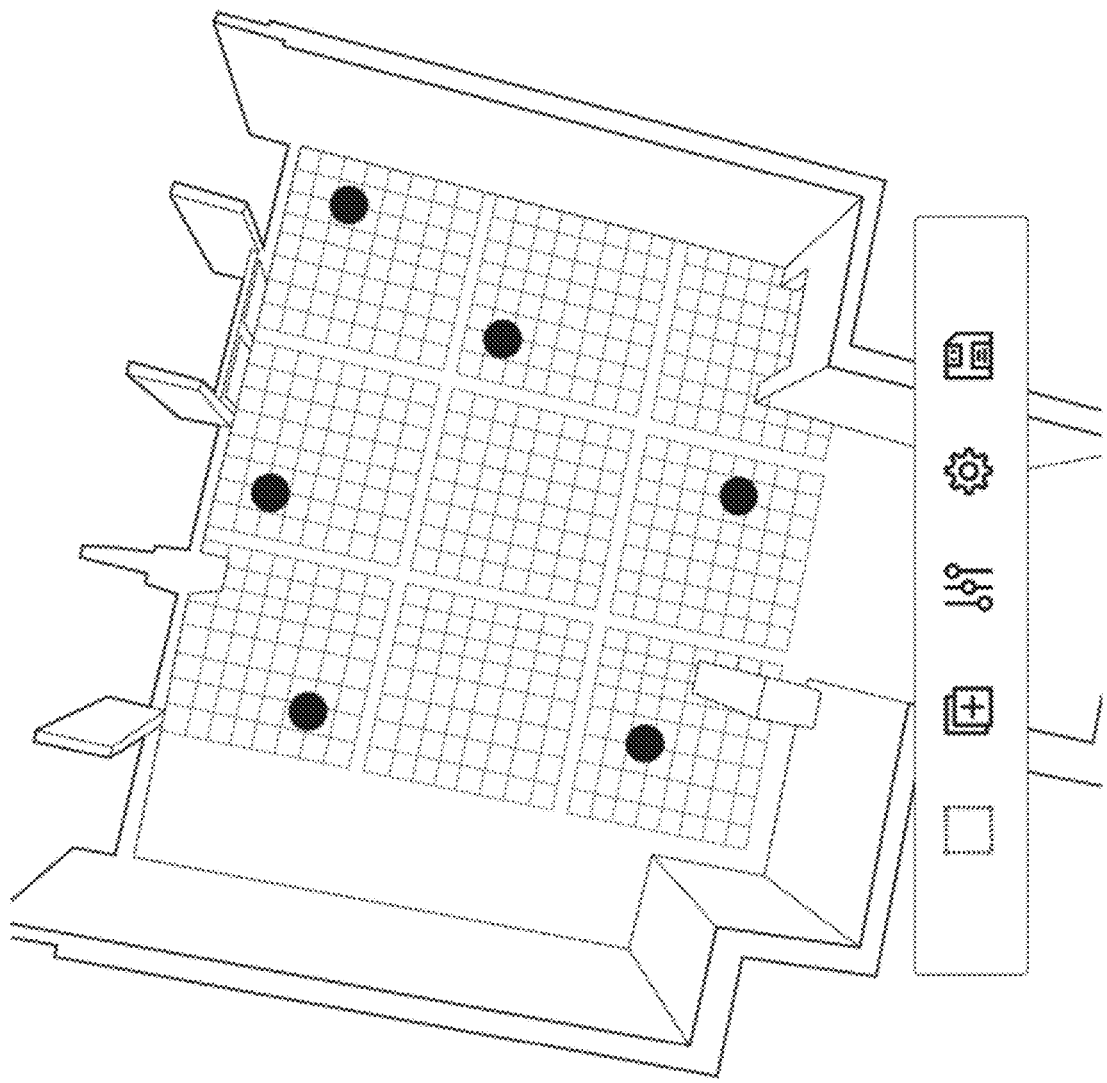
FIG. 5 is an exemplary building layout, in accordance with various embodiments.
Figure 9:
FIG. 9 is an exemplary user interface, showing certain sensor nodes located in spaces that can be tagged with names so that the user understands the contextual information of each sensor node in their equivalent spaces, in accordance with various embodiments.
Figure 9:
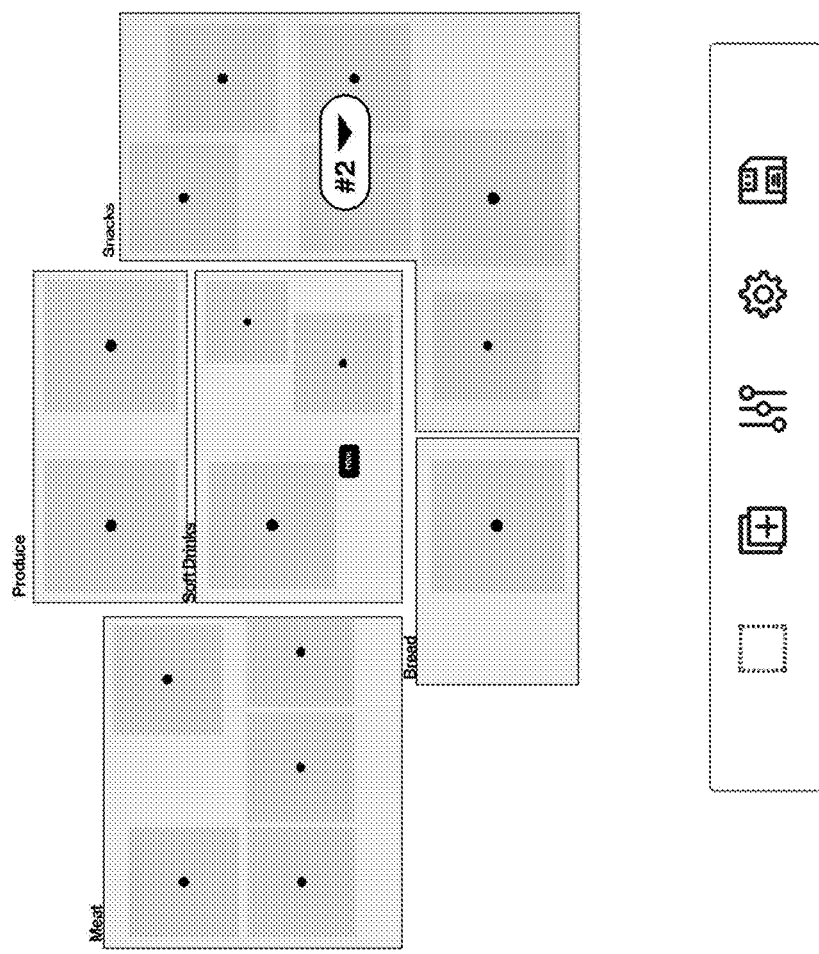

The behavior analytics stem from the fact that, by overlaying the structured network with the actual space, the captured data becomes contextualized. For example, the system can understand the shopping behaviors of moving bodies by cross-referencing the actual trajectories and lingering times captured by the sensor node 102 with an architectural plan that carries information about the location of specific products and aisles, as set forth in FIGS. 5 and 6. In particular, in various embodiments, the user interface 370 allows the user to create a three-dimensional representation of the space in question, as shown in FIGS. 5, 6 and 9. For example, the owner of a grocery store may log information about produce or the location of ice cream refrigerators by naming or "tagging" each sensor node 102 with the specific product that is located within the field of that sensor node 102. As such, if sensor node #1 detects IR energy for 30 seconds, then the system determines that a person lingered within the field of sensor node #1 for 30 seconds. If sensor node #1 is tagged as being in front of the ice cream refrigerators, the system provides data that a person lingered in front of the ice cream refrigerators for 30 seconds. Examples of the system output are shown in FIGS. 4A and 4B.

In various embodiments, and as shown in FIGS. 1A and 1B, each of the plurality of sensor nodes 102 may interface with a module. The module may include, for example, a HTPA 32D Module or HTPA 16D Module. The module may be a radio module. The module may be wireless. The module may be a hardware module.

The sensor node 102 may include a switch 120 (e.g., ALPS) that controls the power to the sensor node 102. The switch 120 may allow the manufacturer of the system to turn off the power to the sensor node 102 to save on the module's battery 130 throughout its transfer or shipment from the manufacturer to the client. After the sensor nodes 102 are delivered to the client, the system may be installed with the switch 120 to the sensor node 102 turned on and left on. If the client shuts down the store or the system for a period of time, the client may use the switch 120 to shut off the sensor nodes 102 to save on battery life. An LED 125 on the sensor node 102 indicates the system status such as, for example, the on mode and the off mode.

Figure 2:
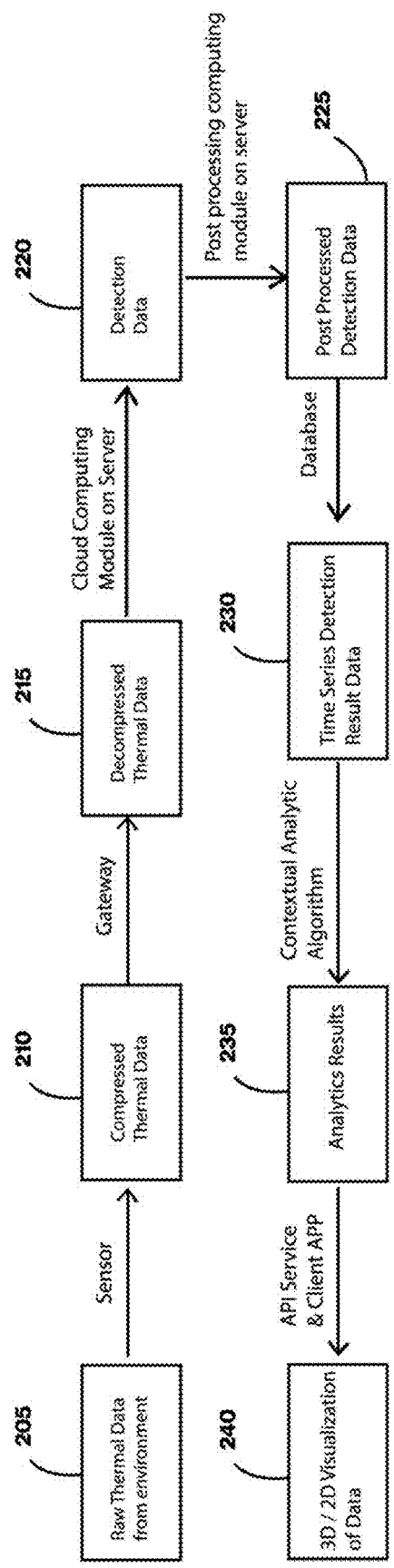
FIG. 2 is an exemplary data flow diagram, in accordance with various embodiments.

A general data flow is set forth in FIG. 2, in accordance with various embodiments. A sensor node 102 may receive raw thermal data from the environment (step 205). The raw thermal data is compressed to create compressed thermal data (step 210). The gateway 135 receives the compressed thermal data from the sensor node 102. The gateway 135 decompresses the compressed thermal data to create decompressed thermal data (step 215). The cloud computing module 350 on the server receives the decompressed thermal data and creates detection data (step 220). The post processing computing module on the server receives the detection data from the cloud computing module 350. The post processing computing module processes the detection data to create post processed detection data (step 225). The post processing computing module sends the post processed detection data to a database 360. The database 360 uses the post processed detection data to create time series detection result data (step 230). The system applies a contextual analytic algorithm to the time series detection result data to create analytics results (step 235). The system applies the API service 380 and client APP to the analytics results to obtain 3D/2D visualization of the data (step 240).

A general system architecture including more details about the data flow is set forth in FIG. 3, in accordance with various embodiments. In the hardware, the sensor node 102 acquires the raw data, then performs edge compression (step 305) and/or edge computing (step 310) to create Message Queuing Telemetry Transport (MQTT) raw data. The cloud computing module 350 on the server receives the MQTT raw data topic 1 from the sensor module 115 via the gateway 135. The cloud computing module 350 applies data stitching and decompression (step 315) to the MQTT raw data topic 1 to create MQTT raw data topic 2. The cloud computing module 350 applies a core algorithm (step 320) to the MQTT raw data topic 2 to create MQTT results topic 1. The cloud computing module 350 applies a world coordinate remap (step 325) to the MQTT results topic 1 to create MQTT results topic 2. The cloud computing module 350 sends the MQTT raw data topic 1, MQTT raw data topic 2, MQTT results topic 1 and MQTT results topic 2 to the database 360. The influxDB receives the data. The database 360 applies contextual analytics (step 330) via a contextual analytic algorithm to the data to create context results (analytics results). The context results are stored in the Dynamo DB. The Dynamo DB also stores the sensor node 102 profile. The database 360 may apply additional contextual analytics in response to updates or additional setup to the sensor module 115 profile. The API 380 obtains the contextual results from the database 360. The API applies real-time raw data, real-time detection, historical raw data, historical detection, historical occupancy, historical traffic and/or historical duration to the data (step 335). The API sends the results to a user interface 370 (e.g., on the client device). The user interface 370 provides a visualization (step 340) (e.g., FIGS. 4A and 4B). The user interface 370 also provides a setup interface (step 345). The setup interface may provide updates to the sensor module 115 profile. The user interface 370 also provides for login functionality (step 350). The login functionality may include AuthO/Firebase.

More particularly, the sensor module 115 may collect the sensor module 115 data, preprocess the data and/or send the collected sensor module 115 data to a gateway 135. The module may include an onboard microprocessor 140. The raw data from the sensor modules 115 may be saved in the RAM of the microprocessor 140. The RAM serves as the temporary memory of the system. The microprocessor 140 is configured to preprocess the raw data by eliminating outliers in the raw data.

In particular, the microprocessor 140 applies defined statistical procedures to the raw data to obtain processed data. In various embodiments, the module conducts the preprocessing using firmware software. The firmware software determines the outliers of the temperature readings statistically. An outlier may be defined by, for example, normalizing the data by subtracting each pixel value from the mean value of the frame. The result is divided with the standard deviation of the frame. The pixel values with three times above or below the standard deviation are removed and replaced using a bilinear interpolation technique, namely with the interpolated product of the adjacent value. The pixel value is replaced instead of being removed so that the input detection is similar before and after the procedure. This technique assists in fixing minor data issues that may be caused due to potential flaws of the sensor module 115 data quality. The combination of the firmware software, circuit design and drivers enable the system to run an algorithm to determine "regions of interest" on each of the data frames, representing human activity under the sensor module 115 view. The regions of interest are not about a pixel with a certain temperature, but rather a pixel with a different temperature (higher or sometimes lower) relative to its surrounding pixels. The regions of interest are then used to compress the processed data and prepare the compressed data for wireless transmission.

The system may include a rolling cache of ten of the data frames to conduct the preprocessing. More specifically, the firmware of the microprocessor 140 may use the most recent ten data frames of the captured data to conduct the pre-processing and post-processing procedures. The system may only process a subset of data because of the limited amount of RAM memory on board (e.g., 8 kb for the application).

The data that passes through the gateway 135 may get uploaded to the cloud computing module 350 on the server. The gateway 135 may be powered by any power source. In various embodiments, the gateway 135 is powered by a 110V outlet. The gateway 135 includes modules to connect to a network (e.g., the internet) via ethernet, wifi and/or cellular connection. As such, the gateway 135 may upload the data to any database 360, server and/or the cloud. The gateway 135 sends pre-processed and compressed data to a computational engine in the cloud computing module 350 which, in turn, outputs results to the database 360*s*. The gateway 135 pulls operational commands from the server in order to execute administrative functions such as software updates, commanding the module to turn the sensor module 115 on and off, changing the sampling frequency, etc.

In various embodiments, the gateway 135 captures the compressed raw data in transmission and sends it to an algorithm running on a processor (e.g., Raspberry Pi 4, Model BCM2711), which will then forward the information to a server (e.g., cloud computing) for further processing.

The processing of the data on the server includes decoding the compressed raw data, normalizing the sensor module 115 temperature data per each sensor module 115's firmware and environmental settings, detecting the object, classifying the object, spatially transforming for a world coordinates system positioning and fusion, multi-sensor module 115 data fusion, object tracking and trajectory generation, cleansing for outlier pixel-level readings, and other post-processing.

In various embodiments, the processing steps work with decompressed raw data. Decoding the compressed raw data optimizes the data transmission as well as the battery 130 consumption levels. Moreover, the normalization of the sensor node 102 temperature to an appropriate temperature range renders the processing steps adaptive to various qualitative and environmental differences (which are expected from sensor node 102 located at different spots in space).

One of the core processing steps of the computational engine of the cloud computing module 350 is the object detection and classification. This processing step detects the positions of objects of interest in the frame, and classifies the object into persons or different categories of objects (e.g., laptop, coffee mug, etc.). The spatial transformation from local to world coordinate system renders the analysis "context-aware." With the spatial transformation, the system may compare and cross-reference the spatial sensor module 115 coverage to the actual floor plan and 3D model of the space in question. Multi-sensor module 115 data fusion unifies the data in the case of missing information or overlapping coverage between multiple sensor modules 115. As mentioned above, with various algorithms, object tracking and trajectory generation distinguishes multiple persons from each other through time. Object tracking and trajectory generation provides a set of trajectories, stemming from the detected objects and persons. The system uses such trajectories to determine a behavior analysis (e.g., lingering position and duration), moving speed and direction. The post-processing step resolves any minor inconsistencies of the detection and tracking algorithm. For example, when there is a missing detection or a gap in the trajectory, the post-processing step assists with stitching information together and mending any broken trajectories.

The system may use a heatic application protocol interface (API), that may be located in the API layer in the system architecture, as set forth in FIG. 3. The API hosts real-time and historical people count data for the spaces that are enhanced with the sensor module 115 solution. Built upon REST, the API returns JSON responses, and supports cross-origin resource sharing. The solution employs standard HTTP verbs in order to perform CRUD operations while, for error-indication purposes, the API returns standard HTTP response codes. Additionally, namespaces are used to implement API versioning while every API request is authenticated using token authentication. The API token, found on the dashboard, is used to authenticate all API endpoints.

This token may be included in the authorization HTTP header, prefixed by the string literal "Token" with a single space separating the two strings. A 403 error message will be generated if the proper authorization header is not involved in the API call. HTTP Authorization Header Authorization: Token YOUR_API_TOKEN. The endpoints use standard HTTP error codes. The response includes any additional information about the error.

The API lists low-level "sensor module 115 events" for a sensor module 115 and a period of time. A timestamp and a trajectory, relative to the sensor module 115 in question, are included in each sensor module 115 event. It is not necessary for the trajectory to be equal to any direction relative to a space (e.g., an entrance or an exit). This call should only be used for testing sensor module 115 performance.

The API provides information regarding the total number of entrances into a specific space on a daily basis for the duration of one week. An analytics object, accompanied by data for that interval and the total number of entrances, is nested in each result's interval object. This call may be used to find out how many people are visiting a space on different days of the week.

The API documents, counts and lists all individual exits from the space of interest over the course of an entire day (or any 24-hour period). Each result carries a timestamp and a direction (e.g., −1). This call is used to find out when people are leaving a space.

The API provides information regarding the current and historical wait time at the entrance of a specific space at any given time during the day. An analytics object accompanied by data for that interval and the total estimated wait duration is nested in each result's interval object. This call is used to find out how many people are waiting in line to get into a space on a different time span.

A webhook subscription allows the receipt of a callback to a specified endpoint on a server. The webhooks may be triggered after every event received from one of the sensor modules 115 for each space that event occurred within. The system may create a webhook, get a webhook, update a webhook or delete a webhook. When a webhook is received, the JSON data will resemble the space and sensor module 115 events in previous sections. It will have additional information: the current count for the associated space and the ID of the space itself. The direction field will be 1 for entrance, and −1 for exit. If any additional headers are configured for the webhook, the additional headers will be included with the POST request. An example of Webhook Data Received may be a single event occurring at a pathway connected to two spaces In various embodiments, the system may include one or more tools to help facilitate installation, help set up the software and hardware, provide more accurate detections, create virtual representations, visualize human movement, test devices and/or troubleshoot devices. The system may include any type of software and/or hardware such as, for example, one or more apps, GUIs, dashboards, APIs, platforms, tools, web-based tools and/or algorithms. The system may be in the form of downloadable software. For example, the software may be in the form of an app downloaded from a website that can be used on a desktop or laptop. The software may also include a web application that can be accessed via a browser. Such web application may be device agnostic and adaptive such that the web application may be accessible on a desktop, laptop or mobile device. The system may be obtained by a license or subscription. One or more login credentials may be used to partially or fully access the system.

As used herein, a space may include the entire layout of an area that may be comprised of one or more rooms. The system functionality may impact different spaces separately. The system may associate multiple rooms within a space. A room may include any walled portion of a space (e.g., conference room) or open area within a space (e.g., hot desk area or corridor). Headcount may include the number of people going in and out of a space or room within a given time range. Occupancy may include the number of people inside a room or space at a given time. Fixtures may include furniture (e.g., chair, desk, etc.) or equipment (e.g., washing machine, stove, etc.).

In general, in various embodiments, the system may plan installations by, for example, visualizing the sensor placement, visualizing the coverage in a space using a 3D drag-and-drop interface, and/or understand the number of sensors and/or hives that may be optimal for a room or space. The system may enable more accurate detections by, for example, analyzing spatial context to differentiate between humans and inanimate objects (and other confounding factors). The system may acquire the spatial context by receiving inputs about, for example, the layout of the space, 3D furniture, rooms and labels/tags. The analysis of the spatial context may involve artificial intelligence and/or machine learning. Using the spatial context, the AI is used to learn about the space so that the AI can accurately identify human presence, behavior, posture and other specific activities. The system may create virtual representations of real places (e.g., across any of the dashboard, Setup App and any other applications that visualize spatial data using the algorithm and API). The virtual representations may be based on the tool receiving labels, tags and/or names for sensors, rooms and spaces. The virtual representations may be shown as unique identifiers in the dashboard and/or API.

In various embodiments, the system may visualize human movement by, for example, showing the current and previous frame (e.g., in the form imagery such as a dot), showing and listing location coordinates within the context of the sensor, virtual space layout and virtual fixtures, showing a person's trajectory, and/or showing a person's posture (e.g., standing, sitting, lying down). The system may test and troubleshoot devices by, for example, showing the user what the sensor is detecting. The user can then confirm that the type and location of the actual object correlates to the visual representation. The system may show what the sensor is detecting in a real-time and/or frame-by-frame representation of human presence and movement within the space. The system may also show when sensors are online, offline, connected and/or disconnected.

In various embodiments, the system may include the functionality to create a space layout. Creating a space layout may involve adding a space and adding a space name. The system then stores the space with its name. The system provides functionality for users to create and manage multiple spaces. Having several separate spaces may be useful when monitoring multiple floors in one building (e.g., 1st floor, 2nd floor), facilities with multiple individual rooms (e.g., senior living apartments), or multiple facilities in separate physical locations (e.g., Boston Lab, San Francisco Lab). As part of the setup, in various embodiments, the system may provide the ability to one or more of: rename a space, add auto alignment, add visualization smoothing, add show local detection, add a tool bar (e.g., main, side, etc.), add a fixture from a library (e.g., piece of furniture from a furniture library), or go back to the project library. The main tool bar may include functions related to the room, sensor, hive, language and/or saving. Exemplary side toolbar functions may include 2D or 3D, show or hide a sensor, show or hide a room, show or hide a fixture, etc. The toolbars and functions may be described as located on a main toolbar or side toolbar, but any of the functionality may be associated with any toolbar.

In various embodiments, the system may include the functionality for the adding of rooms to match or resemble a floor layout. The system may present a control panel (e.g., in response to selecting a room). The control panel may allow the changing of dimensions, tagging certain places or features, and/or selecting a border color for each room. In response to the selection of a room icon, the system may add one or more rooms to a space. In response to auto-alignment being activated, objects (e.g., fixtures, sensors or rooms) that were moved may automatically snap to the edges of nearby objects of the same kind. A chair may be automatically moved next to another object to, for example, make it easier and quicker for a user to arrange objects in a neat and orderly manner to match the floor plans. The system may determine that the moved object is the same kind of object as an existing object based on a similar identifier or label associated with each of the objects. In response to auto-alignment being deactivated, users can move objects freely in increments that may not align with similar objects.

In various embodiments, the system may include the functionality for adding fixtures to the virtual space in the GUI (which may correlate to the fixtures that exist in the physical space). Fixtures may include, for example, furniture or equipment that users can add to the space. Fixtures may allow users to differentiate rooms and allow the users to contextualize the movements seen on the screen. The system may allow users to add fixtures by selecting any of the furniture or equipment icons, then dragging and dropping the fixtures at particular locations in different rooms. The system also provides the functionality for the users to virtually select the fixture, then delete or rotate the fixture using the panel controls. The system also provides the functionality for the users to virtually adjust the size or location of the fixture. In various embodiments, the user may input specific coordinates of the furniture, so the system knows the dimensions and location of the furniture. Moreover, when the user moves a fixture, the system may show the distance between a center point of the fixture and each of the 4 walls of the room it is placed in. The coordinates of the furniture in relation to the entire space may be stored in the system through an API. This way, the user can pull this information from the backend as needed. Users can add as many fixtures as needed in a space or room. The user may layer fixtures or furniture over other fixtures or furniture. Moreover, if a physical table is particularly large, users can use multiple virtual tables to match its size. The system encodes, recognizes, stores and factors in the fixture's presence and coordinates. The system uses such data when determining whether a detection is human and whether the detection should be counted for the occupancy or headcount of a room or space. The system includes functionality (e.g., using APIs and algorithms) that encodes each fixture with a fixture type (e.g., table, door, etc.). The user may select a fixture and fixture type from the icons. The API may save this fixture and its coordinates on the system so that the algorithm can use this information to identify detections and behaviors. In response to placement by the user, the system records the fixture's center point x-y coordinates, fixture type, and rotation from the center point in degrees (e.g., 0, 90, 180, 270). Rotation may include the action of rotating objects (rooms, sensors, fixtures) from its center point by 0, 90, 180, 270 degrees. The rotation may be implemented by selecting a circular arrow to rotate the object. A fixture in the system may be set at a default pointing direction which may be different from the real furniture in the room. The user can rotate the virtual furniture model along the center point of the model to 4 different directions (i.e., 0, 90, 180, 270 degrees from its default direction).

The system may display when people are located on, around or passing by a piece of furniture. The system stores names or icons associated with different fixtures. Such names or icons include factors or rules for the system to consider when analyzing the fixtures. For example, a bed icon may include a rule that a human may be located on the bed, while a table icon may include a rule that a human would not be located on the table. Other examples of fixtures with rules that a human would not be on the fixture includes a table, counter, stove, refrigerator, dishwasher, sink, radiator, counter, and/or washing machine. Other examples of fixtures with rules that a human may be located on or in the fixture include a bed, couch, chair, toilet, and/or shower. The system may infer activities based on the person being located by the furniture for a particular amount of time. For example, if the system detects a person near a TV for an hour, the system may infer that the person liked the show playing on the TV. This location and inference information also provides valuable contextual information to the algorithm to allow the system to infer daily activities and enable more accurate human detections. For example, for daily activities, if a detection of an object (e.g., represented by a purple sphere) is on or within the outline of the bed fixture, then the system may infer that the human is sleeping. The system may then infer the person's sleep time by determining how long the person is located on the bed fixture. As another example, for more accurate human detection, the system may detect both human and non-human heat sources, such as stovetops and laptops. If the detection of a heat source is found to be located in the middle of a fixture such as a table, the system may recognize that this is not a human. Thus, the system may not count this detection as part of the occupancy data (e.g., that a user may receive via an API or dashboard). The system may include the functionality to activate or deactivate the "Show Local Detection" option to view or hide the detections (e.g., purple spheres).

In various embodiments, the system may include the functionality for "Visualization Smoothing". Deactivating the "Visualization Smoothing" causes the detection sphere to be shown exactly how it is detected, frame by frame on specific coordinates. Activating the "Visualization Smoothing" causes the frame-by-frame movement of the purple sphere to be shown with a smooth, continuous animation. More particularly, when the sensor detects an object in the physical space, the system may create an "agent" (e.g., purple sphere) that appears on the corresponding location in the virtual space. The system may also assign a "lifetime" to that agent. The "lifetime" may be a length of time a purple sphere appears in the virtual space to show a detection. In various embodiments, such a lifetime may be set to last for 300 milliseconds, which matches (or is similar to) the interval in which the sensor sends new detections. The system uses the new detections in the new locations in the physical world to update the placement of the purple sphere in the virtual space. As mentioned, the system may display the purple sphere frame by frame or with visualization smoothing. The purple sphere may appear like it is blinking, but the sphere may actually be showing the real-time detection captured by the sensor every 300 milliseconds. The blinking effect is due to the fact that the purple sphere goes from opaque to transparent in its lifetime of 300 milliseconds. If the sphere is more opaque, then the detection may be more recent. If a person is standing still under the actual sensor, the purple sphere will seem like it is blinking in place. If the person is moving under the actual sensor, and visualization smoothing is not activated, the system may show a trail of purple spheres. For example, each of the purple spheres may be going from opaque to transparent in succession in each detection coordinate (or pixel) every 300 milliseconds. With visualization smoothing activated, only one purple sphere appears on the screen and appears to move linearly. During the 300 millisecond lifetime, the system searches for the next detection within a 1 foot radius and "recharges" its lifetime to another 300 milliseconds. This means that the sphere appears continually, moving from one spot to another following the detection coordinates (pixels).

In various embodiments, the system may include the functionality for adding one or more hives and/or heatic sensors. Data from outside the room may be still stored via API, but the outside of the room data may not be shown on the dashboard. The dashboard shows activities and occupancy specific to the rooms within a space. Therefore, the system instructs the user to place sensors and objects in a room. The hive may provide gateway functionality to connect and transmit data from the heatic sensors to a storage location (e.g., the cloud). For example, the hives may connect to a certain number of sensors (e.g., maximum of 12 sensors), then additional hives may be needed for additional sensors. For ease of installation, each hive may be pre-configured with a set of sensors (e.g., the sensor IDs are loaded as sensor data into a database for the hive). The pre-configuration process may include two parts. The sensors may be set to the same NetID as the Hive. This is what enables the sensors to connect to each other. The Hive may obtain the sensor MAC addresses and sensor modes programmed into a configuration file. This is what allows the Hive to correctly manage the sensor frame rates. The system may allow a user to add one or more hives to a space. The system may include the functionality to add a hive to a space by scanning a code (e.g., QR code) or by entering the Hive ID (e.g., found on the sticker underneath the Hive). During the process of the Hive data being added to the system, the system also receives the pre-configured sensor data (because the hive data was pre-configured to include the sensor data). The system uses the sensor data to display the "Sensor" icon for each hive. The system may show sensors from different hives because the sensors may be color coded to show that the sensors belong to a particular group and Hive. The specific implementation may change, but generally may be visually identifiable through the system. In response to receiving a selection of the sensor icon for a hive, all of the sensors associated with that Hive are displayed, so that each sensor may be added to the space. The user may drag and drop each virtual sensor somewhere in the room to record room occupancy, or on a doorway to record headcount of people going in and out of that doorway. Each sensor may be unique and may be identified with a unique address (e.g., MAC address). As such, users should place the virtual sensor in the same location, the same orientation and the same room as that of the corresponding physical sensor.

In various embodiments, the system may include the functionality for the setting and/or calibrating of the virtual heatic sensors. Each virtual heatic sensor may appear on the display (e.g., as a square). In response to the virtual sensor being turned off, the virtual sensor may appear a certain way (e.g., black square) to indicate that the actual sensor is not detecting anything. In response to being turned on, the virtual sensor appears as a grid (e.g., an 8×8 grid made up of 64 squares). Each of the 64 squares may represent each pixel, and the color of each pixel may represent the temperature the actual sensor detects at that point in the grid. The color of each pixel may include a range of shades to indicate the temperature level. For example, the range of shades may be from yellow (lower temperature) to red (higher temperature).

In response to receiving a selection of a virtual sensor, the system displays a control panel (e.g., on the left side of the display). Using the control panel, the system may allow the user to set the virtual sensor height. For example, it may be important for an aisle in a grocery store to be within the field of view, but a janitor's closet can be outside of the field of view. The optimal (and preferred maximum) height of the actual sensor is about 3.2 meters. Such a height may provide maximum coverage and the optimal resolution needed for human detections. Optimal resolution may be based on the algorithm's ability to detect human presence from the heat map image that comes from the sensor. Optimal resolution refers to the resolution at which the system can accurately and reliably detect human presence. The height of the virtual sensor corresponds to the height of the ceiling or the height on the wall where the actual sensor will be attached to. The higher the sensor above the floor, the broader the sensor's floor coverage. The lower the sensor is to the floor, the narrower the sensor's floor coverage. Based on the height, the system determines how much of the floor space the sensor is monitoring (covering).

The system may use the formula $(90\%*2*\tan(30°)*\text{height})\text{\textasciicircum}2$. For example, a ceiling height of 3 m may result in 3.03 m×3.03 m coverage on the floor. A standard supermarket ceiling height is 5.78 m, a standard office ceiling height is 3.12 m and a standard door height is 2.43 m. The system also allows the user to test different heights to confirm that certain areas are within (or outside of) the field of view of the sensor. A sensor height of 110 inches (2.8 m) may provide an effective coverage width of 106 inches (2.7 m), a sensor height of 102 inches (2.6 m) may provide an effective coverage width of 78 inches (2.0 m), a sensor height of 95 inches (2.4 m) may provide an effective coverage width of 63 inches (1.6 m), and a sensor height of 87 inches (2.2 m) may provide an effective coverage width of 56 inches (1.4 m).

In various embodiments, the system may also allow the user to set the virtual sensor direction to conform to how the actual sensor is physically installed to ensure accurate representation between the virtual world (e.g., in the setup app) and the physical world. The sensor direction in both real and virtual worlds must be similar, so that the visible detections also match. For example, a person standing in the northeast corner of the room, must appear on the northeast corner of the corresponding virtual sensor pixels in the setup app. To help match the sensor direction, the physical sensor may include an arrow (e.g., on its mounting plate). When the user adds the physical sensor to the setup app as a virtual sensor, the user matches the direction of the virtual sensor arrow to that of the physical sensor arrow by rotating the virtual sensor.

In various embodiments, the system may include the functionality for the viewing of detections. "Detections" mainly refer to detections of the presence of a human being. The actual sensors may capture a heat map of an area at, for example, 3-5 frames per second. The system may detect human presence by identifying areas of the heat map with about the body temperature (or "heat signature") of a human. The system may represent the detection of the human being on the display (e.g., as a purple sphere). The average normal body temperature for a human being is generally accepted as 98.6° F. (37° C.). However, the normal body temperature can have a wide range, from 97° F. (36.1° C.) to 99° F. (37.2° C.). A temperature over 100.4° F. (38° C.) may imply that the person may have a fever caused by an infection or illness.

In various embodiments, the detection process may include a sensitivity adjustment. The system may receive data about the temperature in a space or room based on a thermometer located within the physical space or room. A sensitivity adjustment may involve improving the ability of the system to detect human presence in environments with temperatures close to that of the human body. The detection is improved by changing the parameter that involves the temperature difference between the detection (human temperature) and the surrounding environment. Increasing sensitivity may involve minimizing this temperature difference, so that the system can more easily detect human presence in, for example, very warm climates. In other words, in colder climates of 65 degrees, the system can more easily determine that any object that is 30 degrees or more warmer than the general room temperature may be a human. However, in warmer climates of 96 degrees, the system may need to detect an object with a temperature delta of 2-3 degrees warmer than the room temperature to consider the object a human.

This detection information may be further processed by the system algorithm to double check and ensure that the final data sent to the API and dashboard are accurate. Such further processing may include additional criteria to filter out detections that do not behave like humans. The system may filter out any object with a temperature lower than a range of human body temperatures (e.g., from 97° F. (36.1° C.) to 99° F. (37.2° C.)). The filtering may include detections that do not move at all (e.g., an appliance like a stove) or stationery detections that seem to be on fixtures that humans are not expected to be on (e.g., in the middle of a table). For example, the system may determine that the heat map showing on a table is more likely to indicate a laptop. Moreover, the system may store coordinates around each fixture such that, detections of objects with coordinates that overlap with the coordinates of any fixture are not counted. In other words, the coordinates around fixtures are blacklisted so as not to count any detections within those coordinates.

In various embodiments, the detections may include headcount. The sensors that determine headcount (headcount sensors) from people entering and leaving a room may be installed above an access doorway of the room (e.g., on the wall facing the inside of the room). The headcount sensors may use data associated with a virtual threshold (or door line) that may be a certain distance from the door. The headcount sensor may only count the detection of a person that crosses the door line. For example, "In" is when a person crosses the door line from left to right, while "Out" is when a person crosses the door line from right to left. The door line reduces false readings from a person that may, for example, put their head inside a door to see what is inside the room, but the person never fully enters the room.

In various embodiments, the system may include the functionality for 2D or 3D view settings. In response to receiving a selection of the 2D/3D button, the system may display all (or any portion) of the entire space in 2D or 3D. The 3D view may provide users who are unfamiliar with the floor plan a more "realistic" spatial context. Such a view may also provide a more intuitive way to understand the space, detections and data. In various embodiments, the system may include the functionality for showing or hiding various features such as, for example, sensors, rooms or fixtures. The system may include the functionality for editing spaces, managing spaces, different viewing modes to visually convey data, etc.

In various embodiments, the system may visually convey data about foot traffic and/or dwell times over a certain period. Foot traffic may be conveyed based on the number of people going "in" and "out" a given doorway (or across a door line) and into a room or space. Foot traffic may also be conveyed by the foot path or trajectory lines of people's movements within a space. The system may include a headcount view where the In and Out numbers may be shown on the virtual layout. The system may also include a trajectory view that shows multiple detections over a period of time, thereby forming a stream of detections in the display. The stream of detections may be used to determine the path of the foot traffic. The system may also show lined traces of movement, wherein the system creates a line through the multiple detections, thereby creating a line that represents the foot traffic path. Dwell time may be the amount of time a person spends in a room or in a set of coordinates in a space. Dwell time may be determined by measuring the amount of time a person is detected in a certain area. The system may infer or identify a unique detection (same person) by location and trajectory, even though the system may not determine if it is the "same" person detected previously. The dwell time may be shown as a heatmap, wherein the darker colors may indicate more time spent in a specific area, and lighter colors may indicate less time spent in a certain area.

In various embodiments, the system may also provide the functionality for posture detection. For example, the system may show when a person is standing, sitting, lying down or has fallen. The key difficulty developing a human pose detection algorithm for the thermal sensor data is the low resolution. Most of the existing algorithms detect key-points (key-points may be points on human skeleton) to detect human poses from images. However, the use of key-points may not be feasible because of the lack of resolution. The present system includes a pose detection algorithm. The algorithm may include sub-modules for extracting a bounding box containing human pixels and detecting the pose of the human inside the bounding box. More specifically, the algorithm may be a deep neural network learning based algorithm. The algorithm may be data driven, wherein the learning algorithm tries to learn a bounding box and human poses from the hand-annotated collected data. Data may be collected as the system runs over time, or, for specific cases, during an initial calibration session. Due to the low resolution, the algorithm may not focus on features based on image intensity. Rather, the algorithm may focus on the distinguishing features of the pattern from the overhead heat signature of a human presence. The system may extract a region (e.g., represented as a rectangle that denotes the 'bounding box') including the human. The bounding box may limit the amount of data to analyze and the box forces the algorithm to focus on the human outline only.

Figure 11A:
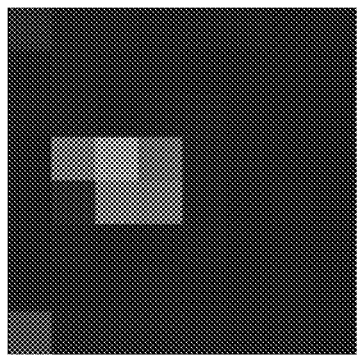
FIGS. 11A-11C shows exemplary heat signature patterns including standing, sitting and lying down poses, in accordance with various embodiments.
Figure 11B:
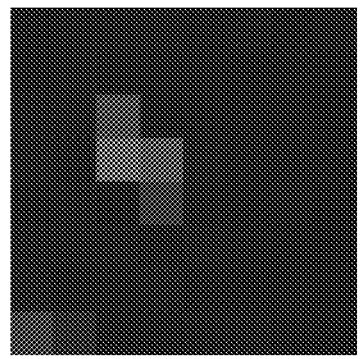
Figure 11C:
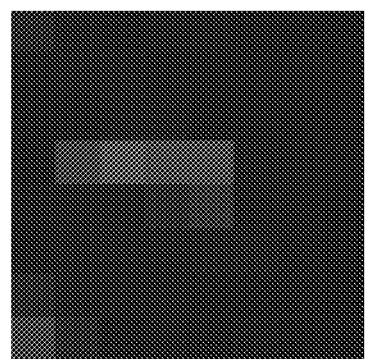

As set forth in FIG. 11, the pattern from human heat signature may be different based on the human pose. For example, FIG. 11A shows a heat signature indicating a standing position, FIG. 11B shows a heat signature indicating a sitting position and FIG. 11C shows a heat signature indicating a lying down position. The system may focus on the extracted bounding box to try to classify the human pose in this step of the algorithm. Using pattern recognition, fuzzy logic, artificial intelligence and/or machine learning, the system may determine the human pose based on similar heat signatures.

The detailed description of various embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and mechanical changes may be made without departing from the spirit and scope of the disclosure. Thus, the detailed description herein is presented for purposes of illustration only and not for purposes of limitation. For example, the steps recited in any of the method or process descriptions may be executed in any order and are not limited to the order presented. Moreover, any of the functions or steps may be outsourced to or performed by one or more third parties. Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. Furthermore, any reference to singular includes plural embodiments, and any reference to more than one component may include a singular embodiment. Although specific advantages have been enumerated herein, various embodiments may include some, none, or all of the enumerated advantages. Systems and methods are provided.

In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the invention. The scope of the invention is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

In various embodiments, software may be stored in a computer program product and loaded into a computer system using a removable storage drive, hard disk drive, or communications interface. The control logic (software), when executed by the processor, causes the processor to perform the functions of various embodiments as described herein. In various embodiments, hardware components may take the form of application specific integrated circuits (ASICs). Implementation of the hardware so as to perform the functions described herein will be apparent to persons skilled in the relevant art(s).

As will be appreciated by one of ordinary skill in the art, the system may be embodied as a customization of an existing system, an add-on product, a processing apparatus executing upgraded software, a stand-alone system, a distributed system, a method, a data processing system, a device for data processing, and/or a computer program product. Accordingly, any portion of the system or a module may take the form of a processing apparatus executing code, an internet based embodiment, an entirely hardware embodiment, or an embodiment combining aspects of the internet, software, and hardware. Furthermore, the system may take the form of a computer program product on a computer-readable storage medium having computer-readable program code means embodied in the storage medium. Any suitable computer-readable storage medium may be utilized, including hard disks, CD-ROM, BLU-RAY DISC®, optical storage devices, magnetic storage devices, and/or the like.

In various embodiments, components, modules, and/or engines of system may be implemented as micro-applications or micro-apps. Micro-apps are typically deployed in the context of a mobile operating system, including for example, a WINDOWS® mobile operating system, an ANDROID® operating system, an APPLE® iOS operating system, a BLACKBERRY® company's operating system, and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

The system and method may be described herein in terms of functional block components, screen shots, optional selections, and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, JAVA®, JAVASCRIPT®, JAVASCRIPT® Object Notation (JSON), VBScript, Macromedia COLD FUSION, COBOL, MICROSOFT® company's Active Server Pages, assembly, PERL®, PHP, awk, PYTHON®, Visual Basic, SQL Stored Procedures, PL/SQL, any UNIX® shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JAVASCRIPT®, VBScript, or the like.

The system and method are described herein with reference to screen shots, block diagrams and flowchart illustrations of methods, apparatus, and computer program products according to various embodiments. It will be understood that each functional block of the block diagrams and the flowchart illustrations, and combinations of functional blocks in the block diagrams and flowchart illustrations, respectively, can be implemented by computer program instructions.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user WINDOWS® applications, webpages, websites, web forms, prompts, etc. Practitioners will appreciate that the illustrated steps described herein may comprise, in any number of configurations, including the use of WINDOWS® applications, webpages, web forms, popup WINDOWS® applications, prompts, and the like. It should be further appreciated that the multiple steps as illustrated and described may be combined into single webpages and/or WINDOWS® applications but have been expanded for the sake of simplicity. In other cases, steps illustrated and described as single process steps may be separated into multiple webpages and/or WINDOWS® applications but have been combined for simplicity.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on the internet server. Middleware may be configured to process transactions between the various components of an application server and any number of internal or external systems for any of the purposes disclosed herein. WEB SPHERE® MQTM (formerly MQSeries) by IBM®, Inc. (Armonk, N.Y.) is an example of a commercially available middleware product. An Enterprise Service Bus ("ESB") application is another example of middleware.

The computers discussed herein may provide a suitable website or other internet-based graphical user interface which is accessible by users. In one embodiment, MICROSOFT® company's Internet Information Services (IIS), Transaction Server (MTS) service, and an SQL SERVER® database, are used in conjunction with MICROSOFT® operating systems, WINDOWS NT® web server software, SQL SERVER® database, and MICROSOFT® Commerce Server. Additionally, components such as ACCESS® software, SQL SERVER® database, ORACLE® software, SYBASE® software, INFORMIX® software, MYSQL® software, INTERBASE® software, etc., may be used to provide an Active Data Object (ADO) compliant database management system. In one embodiment, the APACHE® web server is used in conjunction with a LINUX® operating system, a MYSQL® database, and PERL®, PHP, Ruby, and/or PYTHON® programming languages.

For the sake of brevity, conventional data networking, application development, and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

In various embodiments, the methods described herein are implemented using the various particular machines described herein. The methods described herein may be implemented using the below particular machines, and those hereinafter developed, in any suitable combination, as would be appreciated immediately by one skilled in the art. Further, as is unambiguous from this disclosure, the methods described herein may result in various transformations of certain articles.

In various embodiments, the system and various components may integrate with one or more smart digital assistant technologies. For example, exemplary smart digital assistant technologies may include the ALEXA® system developed by the AMAZON® company, the GOOGLE HOME® system developed by Alphabet, Inc., the HOMEPOD® system of the APPLE® company, and/or similar digital assistant technologies. The ALEXA® system, GOOGLE HOME® system, and HOMEPOD® system, may each provide cloud-based voice activation services that can assist with tasks, entertainment, general information, and more. All the ALEXA® devices, such as the AMAZON ECHO®, AMAZON ECHO DOT®, AMAZON TAP®, and AMAZON FIRE® TV, have access to the ALEXA® system. The ALEXA® system, GOOGLE HOME® system, and HOMEPOD® system may receive voice commands via its voice activation technology, activate other functions, control smart devices, and/or gather information. For example, the smart digital assistant technologies may be used to interact with music, emails, texts, phone calls, question answering, home improvement information, smart home communication/activation, games, shopping, making to-do lists, setting alarms, streaming podcasts, playing audiobooks, and providing weather, traffic, and other real time information, such as news. The ALEXA®, GOOGLE HOME®, and HOMEPOD® systems may also allow the user to access information about eligible transaction accounts linked to an online account across all digital assistant-enabled devices.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; merchant data; financial institution data; and/or like data useful in the operation of the system. As those skilled in the art will appreciate, user computer may include an operating system (e.g., WINDOWS®, UNIX®, LINUX®, SOLARIS®, MACOS®, etc.) as well as various conventional support software and drivers typically associated with computers.

The present system or any part(s) or function(s) thereof may be implemented using hardware, software, or a combination thereof and may be implemented in one or more computer systems or other processing systems. However, the manipulations performed by embodiments may be referred to in terms, such as matching or selecting, which are commonly associated with mental operations performed by a human operator. No such capability of a human operator is necessary, or desirable, in most cases, in any of the operations described herein. Rather, the operations may be machine operations or any of the operations may be conducted or enhanced by artificial intelligence (AI) or machine learning. AI may refer generally to the study of agents (e.g., machines, computer-based systems, etc.) that perceive the world around them, form plans, and make decisions to achieve their goals. Foundations of AI include mathematics, logic, philosophy, probability, linguistics, neuroscience, and decision theory. Many fields fall under the umbrella of AI, such as computer vision, robotics, machine learning, and natural language processing. Useful machines for performing the various embodiments include general purpose digital computers or similar devices.

In various embodiments, the embodiments are directed toward one or more computer systems capable of carrying out the functionalities described herein. The computer system includes one or more processors. The processor is connected to a communication infrastructure (e.g., a communications bus, crossover bar, network, etc.). Various software embodiments are described in terms of this exemplary computer system. After reading this description, it will become apparent to a person skilled in the relevant art(s) how to implement various embodiments using other computer systems and/or architectures. The computer system can include a display interface that forwards graphics, text, and other data from the communication infrastructure (or from a frame buffer not shown) for display on a display unit.

The computer system also includes a main memory, such as random access memory (RAM), and may also include a secondary memory. The secondary memory may include, for example, a hard disk drive, a solid-state drive, and/or a removable storage drive. The removable storage drive reads from and/or writes to a removable storage unit in a well-known manner. As will be appreciated, the removable storage unit includes a computer usable storage medium having stored therein computer software and/or data.

In various embodiments, secondary memory may include other similar devices for allowing computer programs or other instructions to be loaded into a computer system. Such devices may include, for example, a removable storage unit and an interface. Examples of such may include a program cartridge and cartridge interface (such as that found in video game devices), a removable memory chip (such as an erasable programmable read only memory (EPROM), programmable read only memory (PROM)) and associated socket, or other removable storage units and interfaces, which allow software and data to be transferred from the removable storage unit to a computer system.

The terms "computer program medium," "computer usable medium," and "computer readable medium" are used to generally refer to media such as removable storage drive and a hard disk installed in hard disk drive. These computer program products provide software to a computer system.

The computer system may also include a communications interface. A communications interface allows software and data to be transferred between the computer system and external devices. Examples of such a communications interface may include a modem, a network interface (such as an Ethernet card), a communications port, etc. Software and data transferred via the communications interface are in the form of signals which may be electronic, electromagnetic, optical, or other signals capable of being received by communications interface. These signals are provided to communications interface via a communications path (e.g., channel). This channel carries signals and may be implemented using wire, cable, fiber optics, a telephone line, a cellular link, a radio frequency (RF) link, wireless and other communications channels.

As used herein an "identifier" may be any suitable identifier that uniquely identifies an item. For example, the identifier may be a globally unique identifier ("GUID"). The GUID may be an identifier created and/or implemented under the universally unique identifier standard. Moreover, the GUID may be stored as 128-bit value that can be displayed as 32 hexadecimal digits. The identifier may also include a major number, and a minor number. The major number and minor number may each be 16-bit integers.

In various embodiments, the server may include application servers (e.g., WEBSPHERE®, WEBLOGIC®, JBOSS®, POSTGRES PLUS ADVANCED SERVER®, etc.). In various embodiments, the server may include web servers (e.g., Apache, IIS, GOOGLE® Web Server, SUN JAVA® System Web Server, JAVA® Virtual Machine running on LINUX® or WINDOWS® operating systems).

A web client includes any device or software which communicates via any network, such as, for example any device or software discussed herein. The web client may include internet browsing software installed within a computing unit or system to conduct online transactions and/or communications. These computing units or systems may take the form of a computer or set of computers, although other types of computing units or systems may be used, including personal computers, laptops, notebooks, tablets, smart phones, cellular phones, personal digital assistants, servers, pooled servers, mainframe computers, distributed computing clusters, kiosks, terminals, point of sale (POS) devices or terminals, televisions, or any other device capable of receiving data over a network. The web client may include an operating system (e.g., WINDOWS®, WINDOWS MOBILE® operating systems, UNIX® operating system, LINUX® operating systems, APPLE® OS® operating systems, etc.) as well as various conventional support software and drivers typically associated with computers. The web-client may also run MICROSOFT® INTERNET EXPLORER® software, MOZILLA® FIREFOX® software, GOOGLE CHROME™ software, APPLE® SAFARI® software, or any other of the myriad software packages available for browsing the internet.

As those skilled in the art will appreciate, the web client may or may not be in direct contact with the server (e.g., application server, web server, etc., as discussed herein). For example, the web client may access the services of the server through another server and/or hardware component, which may have a direct or indirect connection to an internet server. For example, the web client may communicate with the server via a load balancer. In various embodiments, web client access is through a network or the internet through a commercially-available web-browser software package. In that regard, the web client may be in a home or business environment with access to the network or the internet. The web client may implement security protocols such as Secure Sockets Layer (SSL) and Transport Layer Security (TLS). A web client may implement several application layer protocols including HTTP, HTTPS, FTP, and SFTP.

The various system components may be independently, separately, or collectively suitably coupled to the network via data links which includes, for example, a connection to an Internet Service Provider (ISP) over the local loop as is typically used in connection with standard modem communication, cable modem, DISH NETWORK®, ISDN, Digital Subscriber Line (DSL), or various wireless communication methods. It is noted that the network may be implemented as other types of networks, such as an interactive television (ITV) network. Moreover, the system contemplates the use, sale, or distribution of any goods, services, or information over any network having similar functionality described herein.

The system contemplates uses in association with web services, utility computing, pervasive and individualized computing, security and identity solutions, autonomic computing, cloud computing, commodity computing, mobility and wireless solutions, open source, biometrics, grid computing, and/or mesh computing.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® applets, JAVASCRIPT® programs, active server pages (ASP), common gateway interface scripts (CGI), extensible markup language (XML), dynamic HTML, cascading style sheets (CSS), AJAX (Asynchronous JAVASCRIPT And XML) programs, helper applications, plug-ins, and the like. A server may include a web service that receives a request from a web server, the request including a URL and an IP address (192.168.1.1). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. Web services methods are well known in the art, and are covered in many standard texts. For example, representational state transfer (REST), or RESTful, web services may provide one way of enabling interoperability between applications.

The computing unit of the web client may be further equipped with an internet browser connected to the internet or an intranet using standard dial-up, cable, DSL, or any other internet protocol known in the art. Transactions originating at a web client may pass through a firewall in order to prevent unauthorized access from users of other networks. Further, additional firewalls may be deployed between the varying components of CMS to further enhance security.

Encryption may be performed by way of any of the techniques now available in the art or which may become available—e.g., Twofish, RSA, El Gamal, Schorr signature, DSA, PGP, PKI, GPG (GnuPG), HPE Format-Preserving Encryption (FPE), Voltage, Triple DES, Blowfish, AES, MD5, HMAC, IDEA, RC6, and symmetric and asymmetric cryptosystems. The systems and methods may also incorporate SHA series cryptographic methods, elliptic curve cryptography (e.g., ECC, ECDH, ECDSA, etc.), and/or other post-quantum cryptography algorithms under development.

The firewall may include any hardware and/or software suitably configured to protect CMS components and/or enterprise computing resources from users of other networks. Further, a firewall may be configured to limit or restrict access to various systems and components behind the firewall for web clients connecting through a web server. Firewall may reside in varying configurations including Stateful Inspection, Proxy based, access control lists, and Packet Filtering among others. Firewall may be integrated within a web server or any other CMS components or may further reside as a separate entity. A firewall may implement network address translation ("NAT") and/or network address port translation ("NAPT"). A firewall may accommodate various tunneling protocols to facilitate secure communications, such as those used in virtual private networking. A firewall may implement a demilitarized zone ("DMZ") to facilitate communications with a public network such as the internet. A firewall may be integrated as software within an internet server or any other application server components, reside within another computing device, or take the form of a standalone hardware component.

Any databases discussed herein may include relational, hierarchical, graphical, blockchain, object-oriented structure, and/or any other database configurations. Any database may also include a flat file structure wherein data may be stored in a single file in the form of rows and columns, with no structure for indexing and no structural relationships between records. For example, a flat file structure may include a delimited text file, a CSV (comma-separated values) file, and/or any other suitable flat file structure. Common database products that may be used to implement the databases include DB2® by IBM® (Armonk, N.Y.), various database products available from ORACLE® Corporation (Redwood Shores, Calif.), MICROSOFT ACCESS® or MICROSOFT SQL SERVER® by MICROSOFT® Corporation (Redmond, Wash.), MYSQL® by MySQL AB (Uppsala, Sweden), MONGODB®, DYNAMODB®Redis, Apache Cassandra®, HBASE® by APACHE®, MapR-DB by the MAPR® corporation, or any other suitable database product. Moreover, any database may be organized in any suitable manner, for example, as data tables or lookup tables. Each record may be a single file, a series of files, a linked series of data fields, or any other data structure.

As used herein, big data may refer to partially or fully structured, semi-structured, or unstructured data sets including millions of rows and hundreds of thousands of columns. A big data set may be compiled, for example, from a history of purchase transactions over time, from web registrations, from social media, from records of charge (ROC), from summaries of charges (SOC), from internal data, or from other suitable sources. Big data sets may be compiled without descriptive metadata such as column types, counts, percentiles, or other interpretive-aid data points.

Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); data stored as Binary Large Object (BLOB); data stored as ungrouped data elements encoded using ISO/IEC 7816-6 data elements; data stored as ungrouped data elements encoded using ISO/IEC Abstract Syntax Notation (ASN.1) as in ISO/IEC 8824 and 8825; other proprietary techniques that may include fractal compression methods, image compression methods, etc.

In various embodiments, the ability to store a wide variety of information in different formats is facilitated by storing the information as a BLOB. Thus, any binary information can be stored in a storage space associated with a data set. As discussed above, the binary information may be stored in association with the system or external to but affiliated with the system. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data, in the database or associated with the system, by multiple and unrelated owners of the data sets. For example, a first data set which may be stored may be provided by a first party, a second data set which may be stored may be provided by an unrelated second party, and yet a third data set which may be stored may be provided by a third party unrelated to the first and second party. Each of these three exemplary data sets may contain different information that is stored using different data storage formats and/or techniques. Further, each data set may contain subsets of data that also may be distinct from other subsets.

As stated above, in various embodiments, the data can be stored without regard to a common format. However, the data set (e.g., BLOB) may be annotated in a standard manner when provided for manipulating the data in the database or system. The annotation may comprise a short header, trailer, or other appropriate indicator related to each data set that is configured to convey information useful in managing the various data sets. For example, the annotation may be called a "condition header," "header," "trailer," or "status," herein, and may comprise an indication of the status of the data set or may include an identifier correlated to a specific issuer or owner of the data. In one example, the first three bytes of each data set BLOB may be configured or configurable to indicate the status of that particular data set; e.g., LOADED, INITIALIZED, READY, BLOCKED, REMOVABLE, or DELETED. Subsequent bytes of data may be used to indicate for example, the identity of the issuer, user, transaction/membership account identifier or the like. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the transaction, merchant, issuer, user, or the like. Furthermore, the security information may restrict/permit only certain actions, such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate.

The data, including the header or trailer, may be received by a standalone interaction device configured to add, delete, modify, or augment the data in accordance with the header or trailer. As such, in one embodiment, the header or trailer is not stored on the transaction device along with the associated issuer-owned data, but instead the appropriate action may be taken by providing to the user, at the stand-alone device, the appropriate option for the action to be taken. The system may contemplate a data storage arrangement wherein the header or trailer, or header or trailer history, of the data is stored on the system, device or transaction instrument in relation to the appropriate data.

One skilled in the art will also appreciate that, for security reasons, any databases, systems, devices, servers, or other components of the system may consist of any combination thereof at a single location or at multiple locations, wherein each database or system includes any of various suitable security features, such as firewalls, access codes, encryption, decryption, compression, decompression, and/or the like.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The data may be big data that is processed by a distributed computing cluster. The distributed computing cluster may be, for example, a HADOOP® software cluster configured to process and store big data sets with some of nodes comprising a distributed storage system and some of nodes comprising a distributed processing system. In that regard, distributed computing cluster may be configured to support a HADOOP® software distributed file system (HDFS) as specified by the Apache Software Foundation at www.hadoop.apache.org/docs.

As used herein, the term "network" includes any cloud, cloud computing system, or electronic communications system or method which incorporates hardware and/or software components. Communication among the parties may be accomplished through any suitable communication channels, such as, for example, a telephone network, an extranet, an intranet, internet, point of interaction device (point of sale device, personal digital assistant (e.g., an IPHONE® device, a BLACKBERRY® device), cellular phone, kiosk, etc.), online communications, satellite communications, off-line communications, wireless communications, transponder communications, local area network (LAN), wide area network (WAN), virtual private network (VPN), networked or linked devices, keyboard, mouse, and/or any suitable communication or data input modality. Moreover, although the system is frequently described herein as being implemented with TCP/IP communications protocols, the system may also be implemented using IPX, APPLETALK® program, IP-6, NetBIOS, OSI, any tunneling protocol (e.g. IPsec, SSH, etc.), or any number of existing or future protocols. If the network is in the nature of a public network, such as the internet, it may be advantageous to presume the network to be insecure and open to eavesdroppers. Specific information related to the protocols, standards, and application software utilized in connection with the internet is generally known to those skilled in the art and, as such, need not be detailed herein.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand.

As used herein, "transmit" may include sending electronic data from one system component to another over a network connection. Additionally, as used herein, "data" may include encompassing information such as commands, queries, files, data for storage, and the like in digital or any other form.

Any database discussed herein may comprise a distributed ledger maintained by a plurality of computing devices (e.g., nodes) over a peer-to-peer network. Each computing device maintains a copy and/or partial copy of the distributed ledger and communicates with one or more other computing devices in the network to validate and write data to the distributed ledger. The distributed ledger may use features and functionality of blockchain technology, including, for example, consensus-based validation, immutability, and cryptographically chained blocks of data. The blockchain may comprise a ledger of interconnected blocks containing data. The blockchain may provide enhanced security because each block may hold individual transactions and the results of any blockchain executables. Each block may link to the previous block and may include a timestamp. Blocks may be linked because each block may include the hash of the prior block in the blockchain. The linked blocks form a chain, with only one successor block allowed to link to one other predecessor block for a single chain. Forks may be possible where divergent chains are established from a previously uniform blockchain, though typically only one of the divergent chains will be maintained as the consensus chain. In various embodiments, the blockchain may implement smart contracts that enforce data workflows in a decentralized manner. The system may also include applications deployed on user devices such as, for example, computers, tablets, smartphones, Internet of Things devices ("IoT" devices), etc. The applications may communicate with the blockchain (e.g., directly or via a blockchain node) to transmit and retrieve data. In various embodiments, a governing organization or consortium may control access to data stored on the blockchain. Registration with the managing organization(s) may enable participation in the blockchain network.

Data transfers performed through the blockchain-based system may propagate to the connected peers within the blockchain network within a duration that may be determined by the block creation time of the specific blockchain technology implemented. For example, on an ETHEREUM®-based network, a new data entry may become available within about 13-20 seconds as of the writing. On a HYPERLEDGER® Fabric 1.0 based platform, the duration is driven by the specific consensus algorithm that is chosen, and may be performed within seconds. In that respect, propagation times in the system may be improved compared to existing systems, and implementation costs and time to market may also be drastically reduced. The system also offers increased security at least partially due to the immutable nature of data that is stored in the blockchain, reducing the probability of tampering with various data inputs and outputs. Moreover, the system may also offer increased security of data by performing cryptographic processes on the data prior to storing the data on the blockchain. Therefore, by transmitting, storing, and accessing data using the system described herein, the security of the data is improved, which decreases the risk of the computer or network from being compromised.

In various embodiments, the system may also reduce database synchronization errors by providing a common data structure, thus at least partially improving the integrity of stored data. The system also offers increased reliability and fault tolerance over traditional databases (e.g., relational databases, distributed databases, etc.) as each node operates with a full copy of the stored data, thus at least partially reducing downtime due to localized network outages and hardware failures. The system may also increase the reliability of data transfers in a network environment having reliable and unreliable peers, as each node broadcasts messages to all connected peers, and, as each block comprises a link to a previous block, a node may quickly detect a missing block and propagate a request for the missing block to the other nodes in the blockchain network.

The particular blockchain implementation described herein provides improvements over conventional technology by using a decentralized database and improved processing environments. In particular, the blockchain implementation improves computer performance by, for example, leveraging decentralized resources (e.g., lower latency). The distributed computational resources improves computer performance by, for example, reducing processing times. Furthermore, the distributed computational resources improves computer performance by improving security using, for example, cryptographic protocols.

Any communication, transmission, and/or channel discussed herein may include any system or method for delivering content (e.g. data, information, metadata, etc.), and/or the content itself. The content may be presented in any form or medium, and in various embodiments, the content may be delivered electronically and/or capable of being presented electronically. For example, a channel may comprise a website, mobile application, or device (e.g., FACEBOOK®, YOUTUBE®, PANDORA®, APPLE TV®, MICROSOFT® XBOX®, ROKU®, AMAZON FIRE®, GOOGLE CHROMECAST™, SONY® PLAYSTATION®, NINTENDO® SWITCH®, etc.) a uniform resource locator ("URL"), a document (e.g., a MICROSOFT® Word or EXCEL™, an ADOBE® Portable Document Format (PDF) document, etc.), an "ebook," an "emagazine," an application or microapplication (as described herein), an short message service (SMS) or other type of text message, an email, a FACEBOOK® message, a TWITTER® tweet, multimedia messaging services (MMS), and/or other type of communication technology. In various embodiments, a channel may be hosted or provided by a data partner. In various embodiments, the distribution channel may comprise at least one of a merchant website, a social media website, affiliate or partner websites, an external vendor, a mobile device communication, social media network, and/or location based service. Distribution channels may include at least one of a merchant website, a social media site, affiliate or partner websites, an external vendor, and a mobile device communication. Examples of social media sites include FACEBOOK®, FOURSQUARE®, TWITTER®, LINKEDIN®, INSTAGRAM®, PINTEREST®, TUMBLR®, REDDIT®, SNAPCHAT®, WHATSAPP®, FLICKR®, VK®, QZONE®, WECHAT®, and the like. Examples of affiliate or partner websites include AMERICAN EXPRESS®, GROUPON®, LIVINGSOCIAL®, etc.

The invention claimed is:

1. The method comprising:
   determining, by a sensor system, a temperature of an object in a space, based on infrared (IR) energy data of IR energy from the object;
   determining, by the sensor system, location coordinates of the object in the space;
   comparing, by the sensor system, the location coordinates of the object to location coordinates of a fixture; and
   determining, by the sensor system, that the object is a human being, in response to the temperature of the object being within a range, and in response to the location coordinates of the object being distinct from the location coordinates of the fixture.

2. The method of claim 1, further comprising counting, by the sensor system, the human being in at least one of a headcount or occupancy in the space.

3. The method of claim 1, further comprising counting, by the sensor system, the human being in a headcount in the space, in response to the human being crossing a door line.

4. The method of claim 1, further comprising determining, by the sensor system, that the object is not the human being, in response to at least one of the temperature of the object being outside of the range or the location coordinates of the object overlapping with the location coordinates of the fixture.

5. The method of claim 1, further comprising receiving, by the sensor system, the location coordinates of the fixture in the space.

6. The method of claim 1, wherein the space includes one or more rooms.

7. The method of claim 1, wherein the range of the temperature being between a low temperature of the human being and a high temperature of the human being.

8. The method of claim 1, further comprising determining, by the sensor system, that the object is the human being, based on a fixture type of the fixture.

9. The method of claim 1, further comprising determining, by the sensor system, that the object is the human being, based on an orientation of the fixture.

10. The method of claim 1, further comprising determining, by the sensor system, that the object is the human being, based on movement of the object.

11. The method of claim 1, further comprising auto-aligning, by the sensor system, the object by automatically moving the object to an edge of a nearby object that is similar to the object.

12. The method of claim 1, further comprising adjusting, by the sensor system, a temperature delta between a temperature of the object and a temperature of the space.

13. The method of claim 1, wherein the sensor system includes a plurality of sensor nodes that are replicated by a corresponding plurality of virtual sensor nodes.

14. The method of claim 1, further comprising determining, by the sensor system, a trajectory of the object based on changes of the temperature in pixels, wherein the temperature is projected onto a grid of the pixels.

15. The method of claim 1, further comprising displaying, by the sensor system, the object in a virtual space that replicates the space.

16. The method of claim 1, further comprising displaying, by the sensor system, a trajectory of the object in a virtual space that replicates the space, wherein the trajectory of the object is displayed at least one of frame by frame or with visualization smoothing.

17. The method of claim 1, further comprising displaying, by the sensor system, a dwell time of the object in the space.

18. The method of claim 1, further comprising displaying, by the sensor system, a posture of the human being in the space, based on a pose of the human being.

19. An article of manufacture including a non-transitory, tangible computer readable storage medium having instructions stored thereon that, in response to execution by a sensor system, cause the sensor system to perform operations comprising:
  determining, by the sensor system, a temperature of an object in a space, based on infrared (IR) energy data of IR energy from the object;
  determining, by the sensor system, location coordinates of the object in the space;
  comparing, by the sensor system, the location coordinates of the object to location coordinates of a fixture; and
  determining, by the sensor system, that the object is a human being, in response to the temperature of the object being within a range, and in response to the location coordinates of the object being distinct from the location coordinates of the fixture.

20. A sensor system comprising:
  a processor; and
  a tangible, non-transitory memory configured to communicate with the processor, the tangible, non-transitory memory having instructions stored thereon that, in response to execution by the processor, cause the processor to perform operations comprising:
  determining, by the processor, a temperature of an object in a space, based on infrared (IR) energy data of IR energy from the object;
  determining, by the processor, location coordinates of the object in the space;
  comparing, by the processor, the location coordinates of the object to location coordinates of a fixture; and
  determining, by the processor, that the object is a human being, in response to the temperature of the object being within a range, and in response to the location coordinates of the object being distinct from the location coordinates of the fixture.

* * * * *